(12) United States Patent
Gardinier et al.

(10) Patent No.: US 8,049,013 B2
(45) Date of Patent: Nov. 1, 2011

(54) 5-[4-(AZETIDIN-3-YLOXY)-PHENYL]-2-PHENYL-5H-THIAZOLO[5,4-C]PYRIDIN-4-ONE DERIVATIVES AND THEIR USE AS MCH RECEPTOR ANTAGONISTS

(75) Inventors: Kevin Matthew Gardinier, Fishers, IN (US); David Joseph Garmene, Indianapolis, IN (US); Erik James Hembre, Indianapolis, IN (US); Michael Brunavs, Basingstoke (GB); Helen Jane Szekeres, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 317 days.

(21) Appl. No.: 12/515,432

(22) PCT Filed: Nov. 15, 2007

(86) PCT No.: PCT/US2007/084812
§ 371 (c)(1),
(2), (4) Date: May 19, 2009

(87) PCT Pub. No.: WO2008/076562
PCT Pub. Date: Jun. 26, 2008

(65) Prior Publication Data
US 2010/0069352 A1     Mar. 18, 2010

Related U.S. Application Data

(60) Provisional application No. 60/870,011, filed on Dec. 14, 2006.

(51) Int. Cl.
C07D 513/02     (2006.01)
(52) U.S. Cl. ...................................................... 546/114
(58) Field of Classification Search .................. 546/114
See application file for complete search history.

(56) References Cited

FOREIGN PATENT DOCUMENTS

| WO | WO 03/033476 |   | 4/2003 |
|----|-------------|---|--------|
| WO | WO 2006/066174 | * | 6/2006 |

OTHER PUBLICATIONS

Witty, et al., "Discovery of potent and stable conformationally constrained analogues of the MCH R1 antagonist SB-568849,"Bioorganic and Medicinal Chemistry Letters, vol. 16, No. 18, pp. 4872-4878 (2006).
Dyck, et al., "A Thienopyridazinone-Based Melanin-Concentrating Hormone Receptor 1 Antagonist with Potent in Vivo Anorectic Properties," Journal of Medicinal Chemistry, American Chemical Society, vol. 49, No. 13, pp. 3753-3756 (2006); XP003003117.

* cited by examiner

*Primary Examiner* — Nizal S Chandrakumar
(74) *Attorney, Agent, or Firm* — Francis O. Ginah

(57) ABSTRACT

The present invention relates to a melanin concentrating hormone antagonist compound of formula I: wherein "-----" is absent or is optionally a bond; q is 1 or 2; $R^1$ is independently selected from hydrogen, $—C_1-C_2$ alkyl, halo, hydroxy, $—C_1-C_2$ haloalkyl, $—C_1-C_3$ alkoxy, cyano, $—O—C_3-C_4$ cycloalkyl, and $—OC_1-C_2$ haloalkyl; $R^2$ is selected from the group consisting of hydrogen, $—C_1-C_3$ alkyl, hydroxy, $—C_1-C_3$ alkoxy, cyano, $—C_1-C_2$ haloalkyl, $—OC_1-C_2$ haloalkyl, and halo; $R^3$ is selected from the group consisting of hydrogen, $—C_1-C_4$ alkyl, $—C_2-C_4$ haloalkyl, $—C_2-C_4$ alkylOH, $—C_3-C_6$ cycloalkyl, $—CH_2C_3-C_6$ cycloalkyl, $—C_2-C_4$ alkyl-$O—C_1-C_4$ alkyl, $—C(O)C_1-C_4$ alkyl, $—C(O)C_1-C_4$ haloalkyl, $—CH_2$-thiazole, phenyl, benzyl, tetrahydrothiopyranyl, and tetrahydropyranyl, wherein the cycloalkyl, tetrahydrothiopyranyl, tetrahydropyranyl and thiazolyl group is optionally substituted with one or two groups independently selected from the group consisting of halo, hydroxy, $C_1-C_2$ alkyl, and $—C_1-C_2$ haloalkyl; or a pharmaceutically acceptable salt, enantiomer, diastereomer or mixture thereof, useful in the treating, preventing or ameliorating of symptoms associated with obesity and related diseases.

(I)

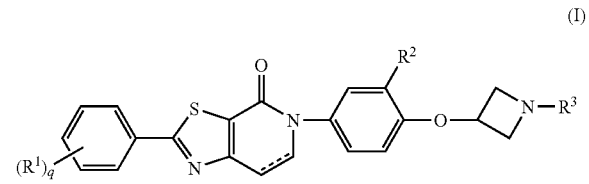

16 Claims, No Drawings

5-[4-(AZETIDIN-3-YLOXY)-PHENYL]-2-PHENYL-5H-THIAZOLO[5,4-C]PYRIDIN-4-ONE DERIVATIVES AND THEIR USE AS MCH RECEPTOR ANTAGONISTS

This application claims the benefit of U.S. Provisional Application Ser. No. 60/870,011, filed 14 Dec. 2006 and PCT Application Serial No. PCT/US2007/084812.

FIELD OF INVENTION

The present invention is in the field of medicine, particularly in the treatment of obesity and diseases related to obesity. More specifically, the present invention relates to selective antagonists of melanin concentrating hormone (MCH) useful for treating, preventing or ameliorating obesity and related diseases.

BACKGROUND OF THE INVENTION

MCH over-expressing transgenic mice are mildly obese, and both MCH−/− and MCHR1−/− mice are characterized by reduced weight gain relative to wild type controls. MCH-induced body weight gain and hyperphagia are absent in MCHR1 null mice. Non-peptide small molecule MCHR1 antagonists attenuate food intake stimulated by MCH. The forgoing support the hypothesis to treat obesity and related diseases with compounds that are effective antagonists of MCHR1.

PCT application number WO 2003/033476A1 discloses compounds reportedly useful as antagonists of the MCH receptor. PCT application number WO 2003/033480A1 discloses compounds reportedly useful as antagonists of the MCH receptor. PCT application WO 2006/066174A1 discloses compounds useful in the treatment, prevention or amelioration of symptoms associated with obesity and related diseases.

Current treatments targeted at obesity have not proven effective for all patients and for sustainable periods of time. Examples of such treatments include various over-the-counter appetite suppressants, various dietary regimens and/or exercise. Therefore, there is a need for new and/or improved therapeutically effective agents useful for treating, preventing and/or ameliorating the effects of obesity.

Antagonists of MCHR1 would be expected to be useful to treat or prevent obesity and related diseases. There is a need to find potent antagonists of MCHR1. There is also a need to find compounds that selectively bind MCHR1 relative to MCHR2. There also exists a need to find MCHR1 antagonists having an improved safety profile over the prior art compounds. The present invention provides such potent, selective MCHR1 antagonists having an improved safety profile for the treatment of obesity and related diseases.

SUMMARY OF INVENTION

The present invention relates to a compound of formula I

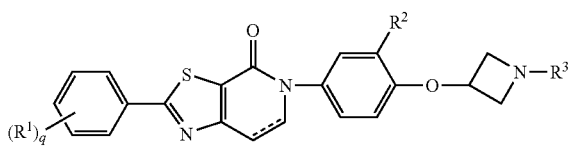

wherein
"-----" is absent or is optionally a bond;
q is 1 or 2;
$R^1$ is independently selected from hydrogen, —$C_1$-$C_2$ alkyl, halo, hydroxy, —$C_1$-$C_2$ haloalkyl, —$C_1$-$C_3$ alkoxy, cyano, —O—$C_3$-$C_4$ cycloalkyl, and —$OC_1$-$C_2$ haloalkyl;
$R^2$ is selected from the group consisting of hydrogen, —$C_1$-$C_3$ alkyl, hydroxy, —$C_1$-$C_3$ alkoxy, cyano, —$C_1$-$C_2$ haloalkyl, —$OC_1$-$C_2$ haloalkyl, and halo;
$R^3$ is selected from the group consisting of hydrogen, —$C_1$-$C_4$ alkyl, —$C_2$-$C_4$ haloalkyl, —$C_2$-$C_4$ alkylOH, —$C_3$-$C_6$ cycloalkyl, —$CH_2C_3$-$C_6$ cycloalkyl, —$C_2$-$C_4$ alkyl-O—$C_1$-$C_4$ alkyl, —$C(O)C_1$-$C_4$ alkyl, —$C(O)C_1$-$C_4$ haloalkyl, —$CH_2$-thiazole, phenyl, benzyl, tetrahydrothiopyranyl, and tetrahydropyranyl, wherein the cycloalkyl, tetrahydrothiopyranyl, tetrahydropyranyl and thiazolyl group is optionally substituted with one or two groups independently selected from the group consisting of halo, hydroxy, $C_1$-$C_2$ alkyl, and —$C_1$-$C_2$ haloalkyl; or a pharmaceutically acceptable salt, enantiomer, diastereomer or mixture thereof.

The present invention also relates to a compound of formula II

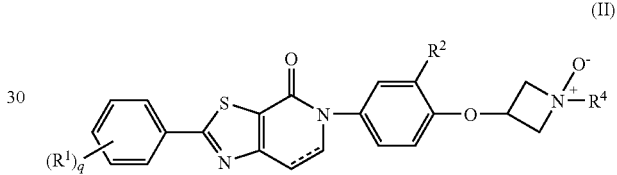

wherein:
"-----" is absent or is optionally a bond;
q is 1, or 2;
$R^1$ is independently selected from hydrogen, —$C_1$-$C_2$ alkyl, halo, hydroxy, —$C_1$-$C_2$ haloalkyl, —$C_1$-$C_3$ alkoxy, cyano, —O—$C_3$-$C_4$ cycloalkyl, and —$OC_1$-$C_2$ haloalkyl;
$R^2$ is selected from the group consisting of hydrogen, —$C_1$-$C_3$ alkyl, hydroxy, —$C_1$-$C_3$ alkoxy, cyano, —$C_1$-$C_2$ haloalkyl, —$OC_1$-$C_2$ haloalkyl, and halo;
$R^4$ is selected from the group consisting of —$C_1$-$C_4$ alkyl, —$C_2$-$C_4$ alkylOH, and —$C_3$-$C_6$ cycloalkyl wherein the cycloalkyl group is optionally substituted with one or two groups independently selected from the group consisting of halo, and —$C_1$-$C_2$ alkyl; or a pharmaceutically acceptable salt, enantiomer, diastereomer or mixture thereof.

The present invention also relates to pharmaceutical compositions comprising a compound of formula I or II.

The present invention also relates to a method for treating or preventing obesity in a patient in need thereof, wherein such treatment or prevention comprises administering to said patient a therapeutically effective amount of a compound of formula I or II in association with a pharmaceutically acceptable carrier, diluent or excipient.

The present invention also relates to a method for selectively antagonizing the binding to the MCHR1 receptors for the treatment of diseases caused, or exacerbated by melanin concentrating hormone.

The present invention provides the use of a compound of formula I or II as an appetite suppressant and/or as a weight loss agent.

The present invention is related to the use of a compound of formula I or II for the manufacture of a medicament for treating obesity and related diseases.

The present invention relates to a compound of formula I or II for use in therapy.

DETAILED DESCRIPTION

For the purposes of the present invention, as disclosed and/or claimed herein, the following terms are defined below.

The term "$C_1$-$C_2$ alkyl" refers to methyl or ethyl groups or radicals thereof.

The term "$C_1$-$C_4$ alkyl" as used herein refers to a straight or branched aliphatic chain of 1 to 4 carbon atoms including but not limited to methyl, ethyl, propyl, iso-propyl, and n-butyl. Unless otherwise stated, the term "alkyl" means $C_1$-$C_4$ alkyl.

The term "$C_3$-$C_6$ cycloalkyl" as used herein refers to a cyclic hydrocarbon radical or group having from 3 to 6 carbon atoms and having no double bonds. $C_3$-$C_6$ cycloalkyl groups include cyclopropyl, cyclobutyl, cyclopentyl, and cyclohexyl.

The term "$C_1$-$C_2$ haloalkyl" refers to a $C_1$-$C_2$ alkyl group substituted with one, two, or three halogen atoms. Examples of $C_1$-$C_2$ haloalkyl include but are not limited to trifluoromethyl, and chloroethyl.

The term "$C_1$-$C_4$ haloalkyl" refers to a $C_1$-$C_4$ alkyl group substituted with one, two, or three halogen atoms as. Examples of $C_1$-$C_4$ haloalkyl include but are not limited to trifluoromethyl, chloroethyl, and 2-chloropropyl.

The term "$C_2$-$C_4$ haloalkyl" refers to a $C_2$-$C_4$ alkyl group substituted with one, two, or three halogen atoms as. Examples of $C_2$-$C_4$ haloalkyl include but are not limited to trifluoroethyl, chloroethyl, and 2-chloropropyl.

The term "$C_1$-$C_3$ alkoxy" group refers to a $C_1$-$C_3$ alkyl moiety connected through an oxy linkage i.e. —$OC_1$-$C_3$ alkyl. Examples of $C_1$-$C_3$ alkoxy groups include methoxy, ethoxy, propoxy, isopropoxy.

The term "$C_2$-$C_4$ alkylOH" as used herein refers to a substituent having the indicated number of carbon atoms terminated by an OH group. For example $C_2$-alkylOH is —$CH_2CH_2OH$.

The term "halo" refers to fluoro, chloro, bromo and iodo.

The term "—$OC_1$-$C_2$ haloalkyl" refers to a $C_1$-$C_2$ alkoxy (i.e. —$OC_1$-$C_2$ alkyl) group having halogen substituents at one or both carbon atoms.

The terms "treating" and "treat", as used herein include restraining, alleviating, ameliorating, slowing, stopping, or reversing the progression or severity of a pathological condition, or sequela thereof.

The term "preventing" as used herein refers to reducing the likelihood that the recipient of a compound of formula I or II will incur or develop any of the pathological conditions, or sequela thereof, described herein.

As used herein, the term "therapeutically effective amount" means an amount of a compound of formula I or II that is sufficient for treating or preventing a condition, or detrimental effects thereof herein described; or an amount of a compound of formula I or II that is sufficient for antagonizing the MCHR1 receptor to achieve the objectives of the invention.

The terms "diseases related to obesity" and "related diseases" as used herein refer to such symptoms, diseases or conditions caused by, exacerbated by, induced by, or related to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression, anxiety, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinemia. Provisional priority application U.S. Ser. No. 60/870,011 discloses a compound of formula

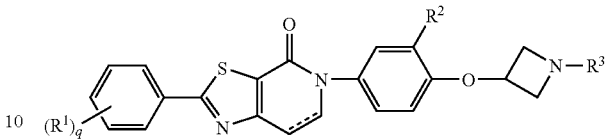

wherein:
"-----" is optionally a bond to form a double bond
q is 0, 1, 2, or 3; wherein other positions on the phenyl ring have hydrogen atoms;
$R^1$ is independently selected from hydrogen, $C_1$-$C_4$ alkyl, halo, hydroxy, $C_1$-$C_4$ haloalkyl, $C_1$-$C_4$ alkoxy, —O—$C_3$-$C_6$ cycloalkyl, and —$OC_1$-$C_4$ haloalkyl;
$R^2$ is is selected from the group consisting of $C_1$-$C_4$ alkyl, hydroxy, —$OC_1$-$C_4$ alkyl, cyano, $C_1$-$C_4$ haloalkyl, —$OC_1$-$C_4$ haloalkyl, and halo;
$R^3$ is selected from the group consisting of hydrogen, $C_1$-$C_4$ alkyl, $C_1$-$C_4$ haloalkyl, $C_2$-$C_4$ alkylOH, $C_3$-$C_6$ cycloalkyl, and $C_2$-$C_4$ alkyl-O—$C_1$-$C_4$ alkyl, —C(O)$C_1$-$C_4$ alkyl, wherein the cycloalkyl group is optionally substituted with one or two groups independently selected from the group consisting of halo, and $C_1$-$C_4$ haloalkyl; or a pharmaceutically acceptable salt thereof.

Certain compounds of formula I or II may also exist as pharmaceutical acid addition salts. Acid addition salts are typically formed by reacting an equivalent amount of acid (based on moles of available basic free pairs of electrons on nitrogen atoms, or a slight excess thereof) with the base compound of the invention. The addition salt product is often isolated as a crystallization product. The crystallization may be spontaneous or may be facilitated by cooling and/or seeding. Pharmaceutically acceptable salts and common methodology for preparing them are known to one of skill in the art. See, e.g. P. Stahl, et al. Handbook of Pharmaceutical Salts: Properties, Selections and Use (VCHA/Wiley-VCH, 200); S. M. Berge, et al., "Pharmaceutical Salts" Journal of Pharmaceutical Sciences, Vol. 66, No. 1, January 1977.

Preferred Compounds of the Invention

Certain compounds of the invention are particularly interesting and preferred. The following listing sets out several groups of preferred compounds
Preferred $R^1$ Groups
Preferred $R^1$ groups are independently selected from the group consisting of hydrogen, halo, hydroxy, —$C_1$-$C_2$ haloalkyl, —$C_1$-$C_3$ alkoxy, —O—$C_3$-$C_4$ cycloalkyl, and —$OC_1$-$C_2$ haloalkyl. A more preferred $R^1$ is chloro, fluoro, methoxy, cyclopropoxy, trifluromethyl, trifluoromethoxy, or cyano. A most preferred $R^1$ group is chloro.
Preferred $R^2$
A preferred $R^2$ group is selected from the group consisting of hydrogen, —$OC_1$-$C_2$ alkyl, cyano, —$OC_1$-$C_2$ haloalkyl, and halo. A more preferred $R^2$ group is selected from the group consisting of hydrogen, methoxy (—OMe), cyano, fluoro, and chloro. Most preferred $R^2$ is methoxy.
Preferred $R^3$ Groups
Preferred $R^3$ groups are independently selected from the group consisting of hydrogen, —$C_1$-$C_4$ alkyl, —$CH_2$cyclopropyl, —$CH_2C_3$-$C_4$ cycloalkyl and —C(O)$C_1$-$C_2$ alkyl, wherein the alkyl and cycloalkyl groups are optionally substituted with one or two groups independently selected from the group consisting of halo, hydroxy, —$C_3$-$C_4$ cycloalkyl, —$C_1$-$C_2$ alkyl, and —$C_1$-$C_2$ haloalkyl. More preferred is an $R^3$ group selected from the group consisting of hydrogen, methyl, cyclopropyl and cyclobutyl.

Preferred $R^4$ Groups

A preferred $R^4$ group is methyl, ethyl, cyclobutyl or cyclopentyl. More preferably, $R^4$ is methyl or cyclobutyl.

A preferred compound of the invention is a compound of formula I wherein
$R^1$ is chloro, methoxy, cyclopropoxy, fluoro, or trifluoromethyl;
q is 1 or 2;
$R^2$ is hydrogen, chloro, —CN or —$OCH_3$; and
$R^3$ is hydrogen, —$CH_3$, —$CH_2CH_2OH$, —$CH_2CH_2F$, —$CH_2CHF_2$, isopropyl, cyclopropyl, —$CH_2$cyclopropyl, or cyclobutyl wherein the cyclopropyl or cyclobutyl group is optionally substituted with one or two groups independently selected from the group consisting of fluoro, methyl, and cyclobutyl.

Also preferred is a compound of formula I wherein
$R^1$ is chloro, methoxy, cyclopropoxy, fluoro, or trifluoromethyl;
q is 1;
$R^2$ is H, —CN or —$OCH_3$; and
$R^3$ is hydrogen, —$CH_3$, —$CH_2CH_2F$, —$CH_2CHF_2$, cyclopropyl, or cyclobutyl wherein the cyclopropyl or cyclobutyl group is optionally substituted with a group selected from the group consisting of fluoro, hydroxy and methyl.

Also preferred is a compound of formula I wherein
$R^1$ is chloro, methoxy, cyclopropoxy, fluoro, or trifluoromethyl;
q is 1;
$R^2$ is chloro or —$OCH_3$; and
$R^3$ is hydrogen, —$CH_3$, —$CH_2CH_2F$, —$CH_2CHF_2$, cyclopropyl, or cyclobutyl wherein the cyclopropyl or cyclobutyl group is optionally substituted with a group selected from the group consisting of fluoro, hydroxy and methyl.

Also preferred is a compound of formula I wherein
$R^1$ is chloro, fluoro, methoxy, or trifluoromethyl;
q is 1;
$R^2$ is —$OCH_3$ or cyano; and
$R^3$ is hydrogen, —$CH_3$, —$CH_2CH_2F$, —$CH_2CHF_2$, cyclopropyl or cyclobutyl wherein the cyclopropyl or cyclobutyl group is optionally substituted with a group selected from the group consisting of fluoro, hydroxy and methyl.

Also preferred is a compound of formula I wherein
$R^1$ is chloro;
q is 1;
$R^2$ is H, $OCH_3$; and
$R^3$ is hydrogen, —$CH_3$, cyclopropyl, or cyclobutyl wherein the cyclopropyl or cyclobutyl group is optionally substituted with a group selected from the group consisting of fluoro, hydroxy and methyl.

Also preferred is a compound of formula I wherein
$R^1$ is chloro, methoxy, cyclopropoxy, fluoro, or trifluoromethyl;
q is 1 or 2;
$R^2$ is H, —CN or —$OCH_3$; and
$R^3$ is hydrogen, —$CH_3$, —$CH_2CH_2OH$, —$CH_2CH_2F$, —$CH_2CHF_2$, isopropyl, cyclopropyl, —$CH_2$cyclopropyl, or cyclobutyl wherein the cyclopropyl or cyclobutyl group is optionally substituted with one or two groups independently selected from the group consisting of fluoro and methyl.

Also preferred is a compound according of formula I wherein
$R^1$ is chloro;
q is 1;
$R^2$ is H, —$OCH_3$; and
$R^3$ is hydrogen, —$CH_3$, cyclopropyl, or cyclobutyl wherein the cyclopropyl or cyclobutyl group is optionally substituted with a group selected from the group consisting of fluoro, hydroxy and methyl.

Also preferred is a compound of formula II wherein
$R^1$ is chloro, methoxy, cyclopropoxy, fluoro, or trifluoromethyl;
q is 1;
$R^2$ is —CN or —$OCH_3$; and
$R^4$ is $CH_3$.

Also preferred is a compound of formula II wherein
$R^1$ is chloro, methoxy, cyclopropoxy, fluoro, or trifluoromethyl;
q is 1;
$R^2$ is —$OCH_3$; and
$R^4$ is $CH_3$.

The compounds of formula (I) or (II) can be prepared by a variety of procedures known in the art and those described below. However, the following discussion is not intended to be limiting to the scope of the present invention in any way. For example, the specific synthetic steps for each of the routes described may be combined in different ways, or in conjunction with steps from different schemes, to prepare additional compounds of formula (I) or (II). The products of each step in the Schemes below can be recovered by conventional methods including extraction, evaporation, precipitation, chromatography, filtration, trituration, crystallization, and the like.

As used herein, the following terms have the meanings indicated: "MeOH" refers to methanol; "EtOH" refers to ethanol; "EtOAc" refers to ethyl acetate; "DMF" refers to dimethylformamide; "DMSO" refers to dimethyl sulfoxide; "TFA" refers to trifluoroacetic acid; "$Et_2O$" refers to diethyl ether; "THF" refers to tetrahydrofuran; "LDA" refers to lithium diisopropylamide; "n-BuLi" refers to n-butyl lithium; "p-TsOH" refers to p-toluenesulfonic acid; "tert-BuOK" refers to potassium tert-butoxide; "DIBAL" refers to diisobutylaluminium hydride; "TEMPO" refers to 2,2,6,6-tetramethyl-1-piperidinyloxy, free radical; "DEAD" refers to diethyl azodicarboxylate; "DIAD" refers to diisopropyl diazodicarboxylate; "tBOC" or "Boc" refers to tert-butoxycarbonyl; "TLC" refers to thin layer chromatography; and "HPLC" refers to high performance liquid chromatography Scheme 1

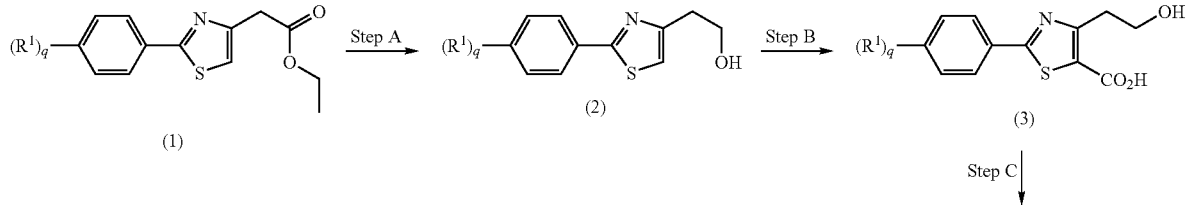

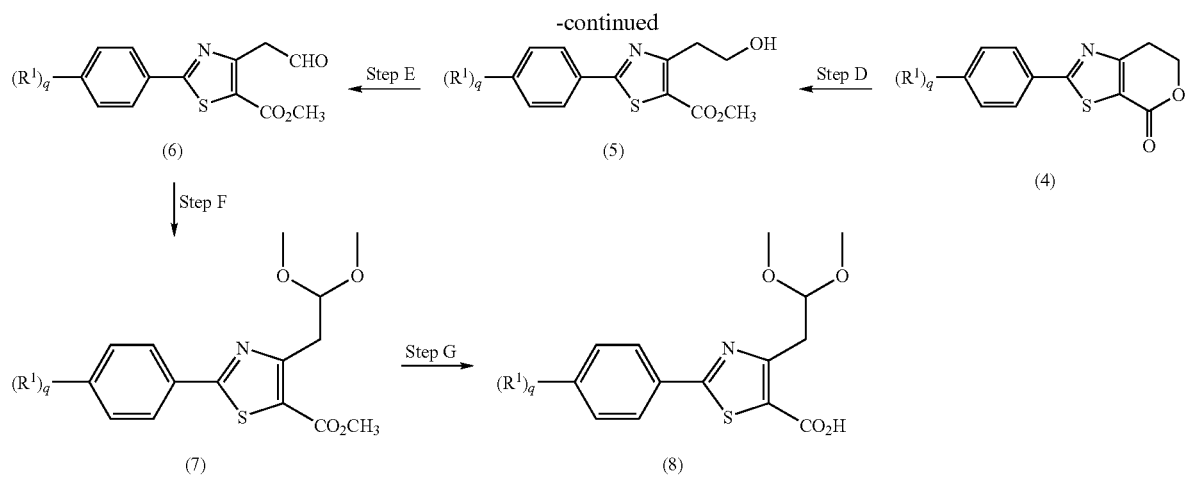

Formation of an intermediate of formula (8) can be carried out in accordance with reactions as depicted in Scheme 1. An appropriate compound of formula (8) is one in which $(R^1)_q$, is as defined for formula I.

In Scheme 1, Step A, a thiazole acetic acid ester of formula (1) is reduced to a thiazole ethanol of formula (2). As will be apparent to the skilled artisan there are numerous reducing agents, such as $LiAlH_4$, $NaBH_4$, $LiBH_4$, and the like, suitable for use in such a transformation. The preferred method uses DIBAL, in an aprotic solvent, such as ether, toluene, or preferably THF, at a temperature of about −80 to 60° C.

In Scheme 1, Step B, a thiazole of formula (2) is carboxylated to form a thiazole carboxylic acid of formula (3). For example, the thiazole (2) is treated with 2 to 3 eq. of a suitable base such as LDA, lithium bis(trimethylsilyl)amide, or preferably n-butyl lithium, in THF or diethyl ether, at a temperature of about −80 to −70° C. over about 2 to 4 h. The resulting dianion is then treated with a solution of $CO_2$ gas in THF or diethyl ether to obtain the thiazole carboxylic acid of formula (3).

In Step C, a thiazole carboxylic acid of formula (3) is dehydrated under anhydrous conditions to form a thiazole lactone of formula (4). For example, a solution of a carboxylic acid of formula (3) in anhydrous toluene or benzene is treated with an acid catalyst, such as para-toluenesulfonic acid and heated to reflux for 4 to 24 h to cyclize to a lactone of formula (4). The use of a Dean-Stark trap accelerates the reaction by removing water as it is produced.

In Scheme 1, Step D, a thiazole lactone of formula (4) is trans-esterified to an ester alcohol of formula (5) using a mineral acid, such as concentrated sulfuric acid, in the presence of methanol. Subsequently, in Step E, an alcohol of formula (5) is oxidized to an aldehyde of formula (6). It will be recognized by the skilled artisan that there are numerous methods for such an oxidation. The preferred method uses TEMPO in an inert solvent, such as dichloromethane, in the presence of potassium bromide, sodium hypochlorite, and sodium bicarbonate.

In Scheme 1, Step F, an aldehyde of formula (6) is converted to an acetal of formula (7). There are various methods for acetal formation available to one skilled in the art. The preferred conditions use an acidic ion exchange resin with trimethyl orthoformate in MeOH. In Step G, an acetal-ester of formula (7) is hydrolyzed to an acid of formula (8) using an inorganic base, such as sodium hydroxide in a suitable polar solvent, such as ethanol.

As will be readily appreciated, a compound of formula (1) can be prepared by methods similar to those described herein using procedures that are well-known and appreciated in the art. For example, compounds of formula (1) are prepared by cyclization of a thioamide with an haloacetoacetate. If not commercially available thioamides are easily prepared from substituted benzamides using methods known in the art, such as with Lawesson's reagent or phosphorous pentasulfide.

Scheme 2

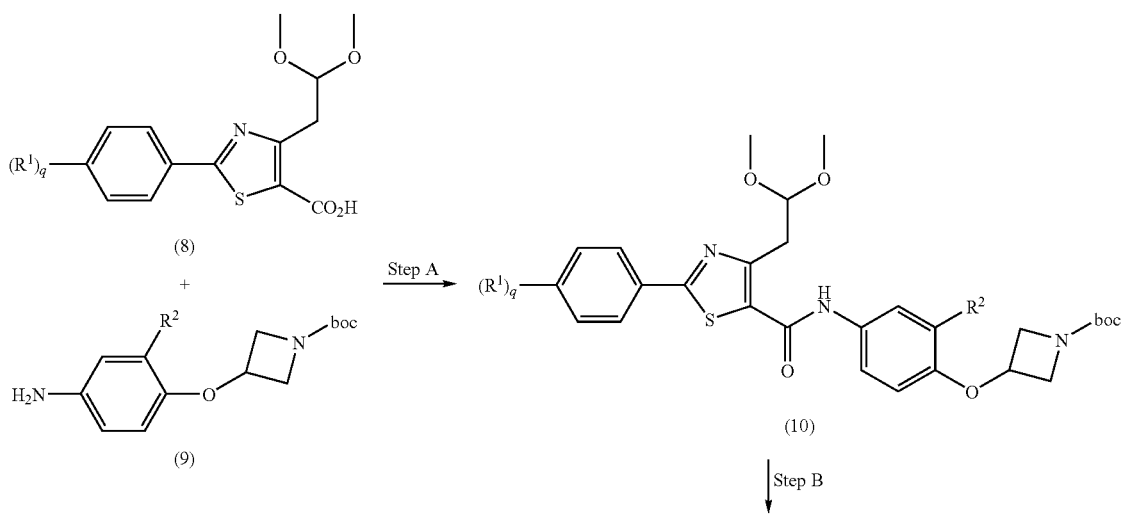

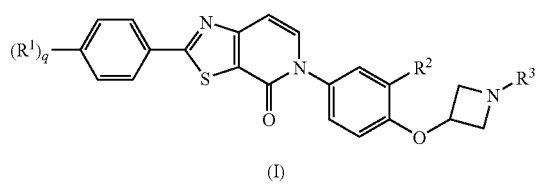 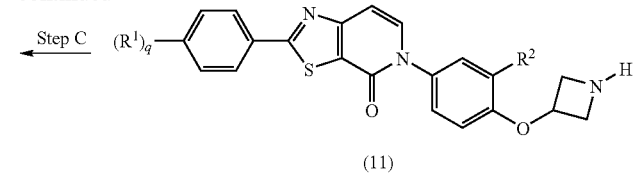

Formation of compounds of formula (I), can be carried out in accordance with methods depicted in Scheme 2. An appropriate compound of formula (8) is one in which $(R^1)_q$, is as defined in formula (I) and an appropriate compound of formula (9) is one in which $R^2$ is as defined in formula (I).

In Scheme 2, Step A, an acid of formula (8) is acylated with an amine of formula (9). It will be well recognized by the skilled artisan that there are a variety of methods available for acylation of carboxylic acids. The preferred method uses 1-hydroxybenzotriazole hydrate and 1-(3-dimethylaminopropyl)-3-ethylcarbodiimide hydrochloride in the presence of an amine, such as diisopropylethylamine, in an inert solvent such as dichloromethane, acetonitrile, or preferably THF.

In Scheme 2, Step B, a thiazole-amide of formula (10) undergoes intramolecular cyclization to form a thiazole-pyridinone of formula (11) with concomitant loss of the tBOC protecting group to give an N-unsubstituted azetidine. The cyclization is performed in an inert solvent such as ethanol in the presence of an inorganic acid, such as concentrated HCl, and heated at the reflux temperature of the solvent for 1 to 24 h.

The N-unsubstituted azetidine of formula (11), while itself a desired product for purposes of the invention, can also be substituted to obtain other compounds of the invention. For example, in Scheme 2, Step C, the unsubstituted azetidine (11) is reductively alkylated with formaldehyde, acetone, cyclobutanone or other aldehydes and ketones using sodium cyanoborohydride or sodium triacetoxy borohydride. The azetidine (11) is also reductively alkylated with ketals or acetals such as [(1-ethoxycyclopropyl)oxytrimethylsilane or 2,5-dihydroxy-1,4-dioxane. Such ketones, aldehydes, ketals, or acetals can be optionally substituted using procedures known in the art. In addition, the azetidine (11) is acylated with optionally substituted acyl chlorides, chloroformates, or activated carboxylic acids, such as trifluoropropionyl chloride or acetyl chloride.

As will be readily appreciated, compounds of formula (9) can be prepared by methods and procedures that are described herein, or that are known in the art. For example, compounds of formula (9) are prepared by nucleophilic aromatic substitution of a fluoro or chloro-nitrobenzene with commercially available 3-hydroxy-azetidine-1-carboxylic acid tert-butyl ester. Subsequent reduction of the nitro group to the amine provides the aniline (9).

Scheme 3

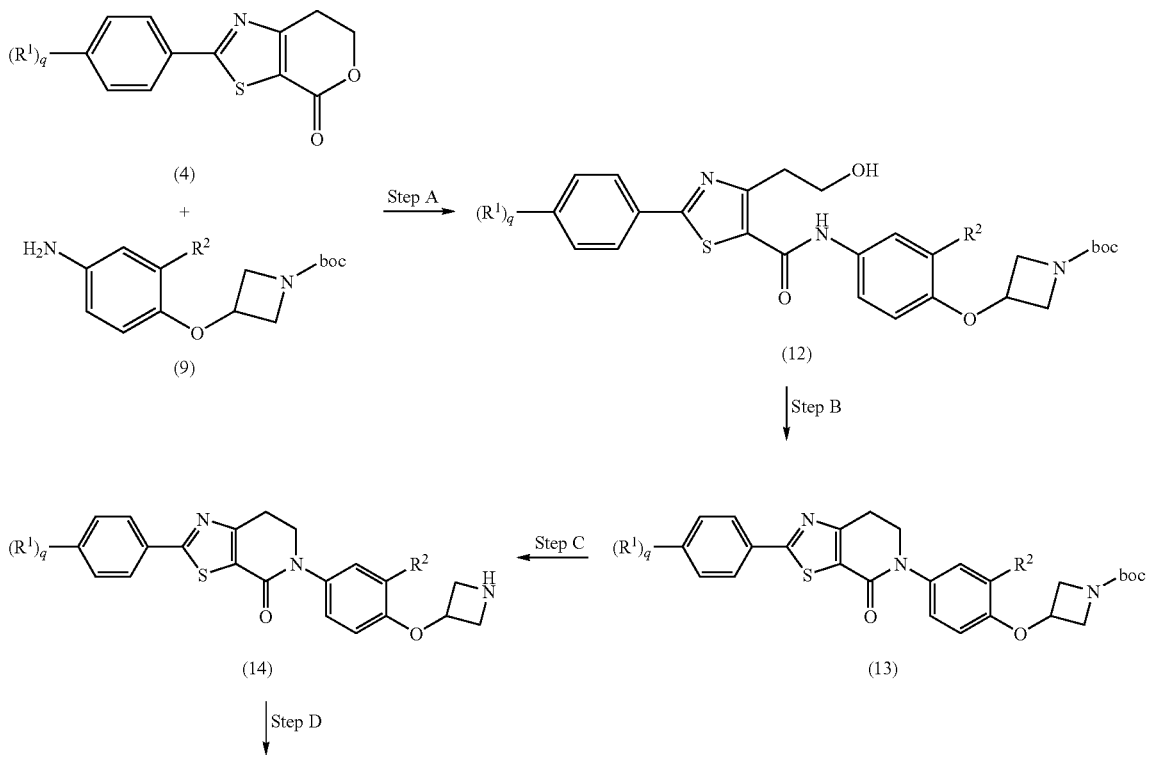

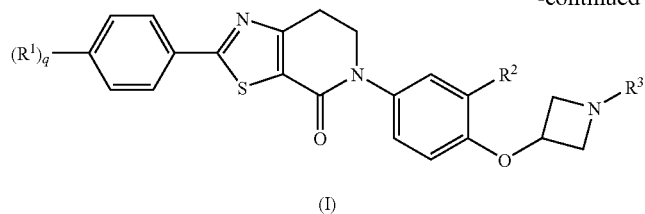
(I)

Formation of compounds of formula (I), can be carried out in accordance with methods depicted in Scheme 3. An appropriate compound of formula (4) is one in which $(R^1)_q$, is as defined in formula (I) and an appropriate compound of formula (9) is one in which $R^2$ is as defined in formula (I).

In Scheme 3, Step A, a thiazole lactone of formula (4) is reacted with an amine of formula (9), using a typical Weinreb protocol (Basha, Anwer; Lipton, M.; Weinreb, Steven M. Tetrahedron Letters, 1977, 48, 4171-4174) to form an amide of formula (12). For example, amine (9) is dissolved in an aprotic solvent, such as $CH_2Cl_2$ or preferably toluene, and treated with a 2-2.5M solution of trimethylaluminum in toluene. The resulting solution is stirred at a temperature from about 0° C. to room temperature for about 5 to 60 minutes, and then treated with a thiazole lactone of formula (4). The resulting solution is stirred at a range of between about room temperature and 110° C. for about 3 to 24 hours to give an amide of formula (12).

In Scheme 3, Step B, the thiazole amide of formula (12) is cyclized using Mitsunobu conditions (Maligres, P. E.; et. al. *J. Het. Chem.* 2003, 40(2), 229-241) to form a thiazole lactam of formula (13). For example, the amide of formula (12) is treated with a trialkyl- or triarylphosphine such as $Me_3P$, $Ph_3P$, or preferably $Bu_3P$, and a dialkylazo-dicarboxylate such as DEAD or DIAD. The reaction is performed in an inert solvent, such as toluene, $CH_2Cl_2$, or preferably THF.

In Step C, the tBOC thiazole lactam azetidine of formula (13) is deprotected to the unsubstituted azetidine of formula (14). Common deprotection conditions for removing a tBOC group are well know by those skilled in the art and can be found in the text of T. W. Green and P. G. M. Wuts in "Protective Groups in Organic Synthesis", John Wiley & Sons, Inc., 1991, 328-330. Preferred conditions use trifluoroacetic acid or alternatively 37% hydrochloric acid in a solvent of n-propanol at room temperature to about 90° C.

The unsubstituted azetidine of formula (14) while itself a desired product for purposes of the invention, can also be substituted to obtain other compounds of the invention as shown in Scheme 3, Step D, in a manner similar to that described in Scheme 2, Step C.

Scheme 4

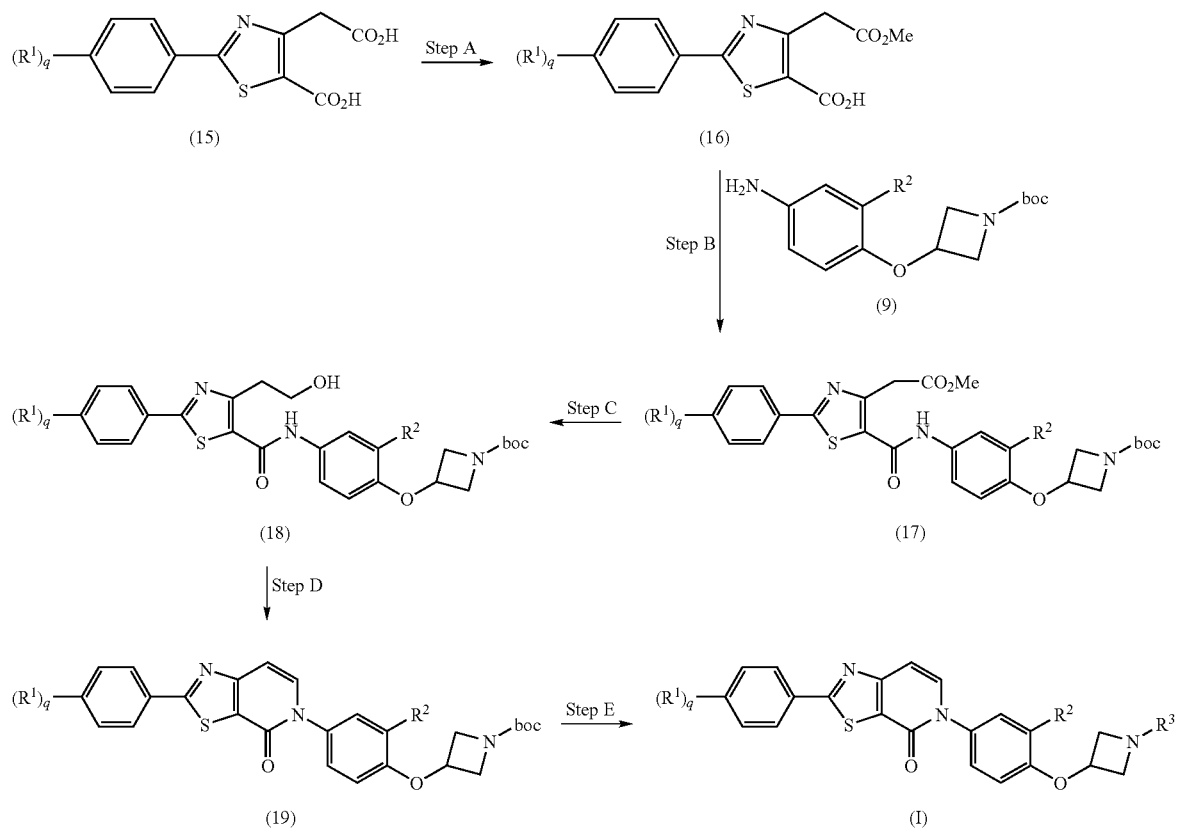

An alternate route for the formation of compounds of formula (I), can be carried out in accordance with methods depicted in Scheme 4.

In Scheme 4, Step A, a thiazolyl dicarboxylic acid of formula (15) is selectively esterified to an thiazolyl ester-acid of formula (16). The esterification conditions use an alcoholic solvent, such as methanol, in the presence of a mineral acid, such as sulfuric acid at a temperature of about 50° C. to the reflux temperature of the solvent.

In Scheme 4, Step B, a thiazolyl ester-acid of formula (16) is acylated with an amine of formula (9) to give a thiazolyl ester-amide of formula (17). It will be recognized by the skilled artisan that there are a variety of methods available for acylation of carboxylic acids. The preferred method uses 1-propanephosphonic acid cyclic anhydride as a coupling reagent, in an inert solvent, such as THF, in the presence of an organic amine, such as N-methylmorpholine.

In Step C, an ester-amide of formula (17) is reduced to an alkylhydroxy-amide of formula (18). One skilled in the art will recognize that there are a variety of methods to reduce esters to alcohols such as lithium aluminum hydride, diisobutylaluminum hydride, borane-methyl sulfide complex, or lithium borohydride. The preferred conditions use lithium borohydride in an inert solvent such as THF.

In Scheme 4, Step D, an alkylhydroxy amide of formula (18) is cyclized to a thiazole-pyridinone of formula (19). The alcohol is first oxidized to the formaldehyde using sulfur trioxide pyridine complex, which then cyclizes with the amide in situ to form the pyridinone. The reaction proceeds in an inert solvent, such as DMSO at room temperature to about 100° C.

In Step E, a thiazole-pyridinone azetidine of formula (19) is deprotected using methods previously described for Scheme 3, Step D. The resulting unsubstituted azetidine is further reacted to give compounds of the invention, depicted in formula (I), as previously described for Scheme 2, Step C.

As will be readily appreciated, compounds of formula (15) can be prepared by methods and procedures that are described herein, or that are known in the art. For example, 3-oxo-pentanedioic acid diethyl ester can be chlorinated with sulfuryl chloride and then subsequently reacted with a thiobenzamide to provide the 2-phenyl-4-ethoxycarbonylmethyl-thiazole-5-carboxylic acid ethyl ester. The diethyl ester is then hydrolyzed to the diacid of formula (15).

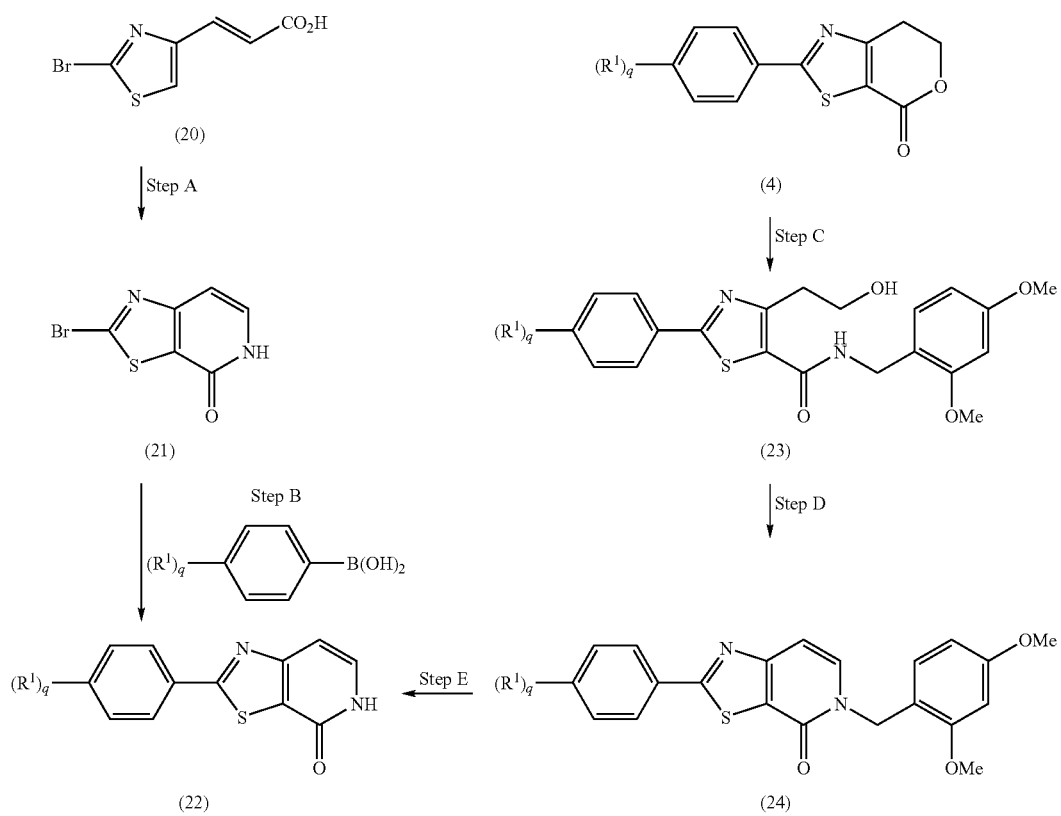

Scheme 5

Formation of an intermediate of formula (22) can be carried out in accordance with reactions as depicted in Scheme 5. An appropriate compound of formula (22) is one in which $(R^1)_q$, is as defined for formula I.

In Scheme 5, Step A, 3-(2-bromo-thiazol-4-yl)-acrylic acid (20) is converted to an acyl azide, which subsequently undergoes a Curtius rearrangement to the isocyanate which cyclizes to bromo thiazolo-pyridinone of formula (21). The acid chloride is conveniently generated with oxalyl chloride in an inert solvent, such as dichloromethane. Following evaporation the acid chloride is reacted with sodium azide in a solvent mixture such as water/acetone/dioxane or THF to give the acyl azide. After workup the acyl azide is heated to a high temperature of about 180 to 250° C. in Dowtherm® A and dioxane for about 30 minutes to 4 hours. The isocyanate is formed in situ and undergoes intramolecular reaction with the thiazole to form the bromo thiazolo-pyridinone of formula (21).

In Step B, the bromo thiazolo-pyridinone of formula (21) is reacted with a phenyl boronic acid to provide a phenyl thiazolo-pyridinone of formula (22) in a Suzuki cross-coupling reaction. The skilled artisan will recognize that there are a variety of conditions useful for facilitating such cross-coupling reactions. The reaction conditions make use of a suitable solvent such as dioxane, toluene, or dimethoxyethane with the addition of ethanol and water. A solution of an inorganic base is added, such as sodium or potassium carbonate. The reaction takes place in the presence of a palladium catalyst, such as tetrakistriphenyl phosphine palladium (0) under an inert atmosphere at temperature of about 70 to 100° C. for about 8 to 24 hours.

Alternatively, a phenyl thiazolo-pyridinone of formula (22) can be obtained from a lactone of formula (4) as shown in Steps C, D, and E.

In Scheme 5, Step C, a lactone of formula (4) is reacted with 2,4-dimethoxybenzylamine in a Weinreb protocol as described for Scheme 3, Step A to provide a thiazole-amide of formula (23).

In Step D, the amide of formula (23) is cyclized to the benzyl thiazolo-pyridinone of formula (24). The alcohol is oxidized to the aldehyde using 1-hydroxy-1-oxo-1H-benzo[d][1,2]iodoxol-3-one and then subsequently reacted with the amide. The reaction takes place in an inert solvent, such as ethyl acetate, at a temperature of 40° C. to the refluxing temperature of the solvent.

In Step E, the 2,4-demethoxybenzyl protecting group is removed using neat TFA at a temperature of 50 to 100° C. to obtain a thiazolo-pyridinone of formula (22).

It will be appreciated, that a bromothiazole of formula (20) can be prepared by methods and procedures that are described herein, or that are known in the art. For example, 2-bromothiazole-4-carbaldehyde can be extended to the acrylic acid methyl ester with methyl(triphenylphosphoranylidene)acetate in a Wittig reaction followed by hydrolysis to obtain the bromothiazole acrylic acid of formula (20).

or (25b) to give a thiazolo-pyridinone of formula (19) or formula (I). The reaction takes place in an inert solvent such as THF, or preferably dioxane with an inorganic base added, such as cesium carbonate. A copper catalyst is used, such as copper (I) iodide in the presence of sym-dimethylethylene diamine. The reaction is heated at a temperature of about 70° C. to the reflux temperature of the solvent.

In Step B, it is recognized that the protected azetidine of formula (19) can be easily converted to the final products of formula (I) as described previously, such as in Scheme 3, Steps C and D.

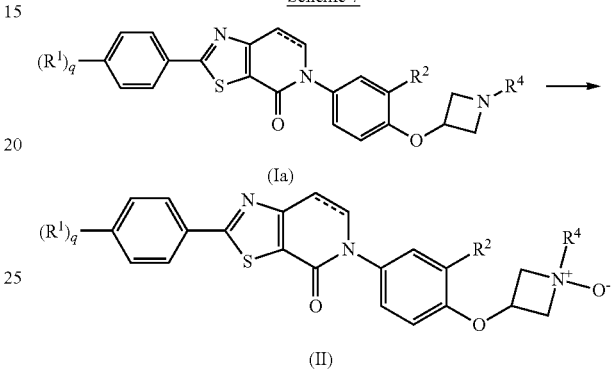

Formation of compounds of formula (II), can be carried out in accordance with the method depicted in Scheme 7, wherein $R^4$ is as defined for formula (II).

An azetidine of formula (Ia) is oxidized to an azetidine N-oxide of formula (II) using m-chloroperoxybenzoic acid in an inert solvent such as dichloromethane.

$^{125}$I-MCH binding and functional GTPγ$^{35}$S binding assays are used to demonstrate potency of the compounds of the present invention as MCHR1 antagonists. One of skill in the art is able to perform both the $^{125}$I-MCH binding and functional GTPγ$^{35}$S binding assays using the procedures herein or procedures disclosed in the art. For binding assay, see for example, Macdonald, D., et al., 2000. *Molecular characterization of the melanin-concentrating hormone/receptor complex: identification of critical residues involved in binding*

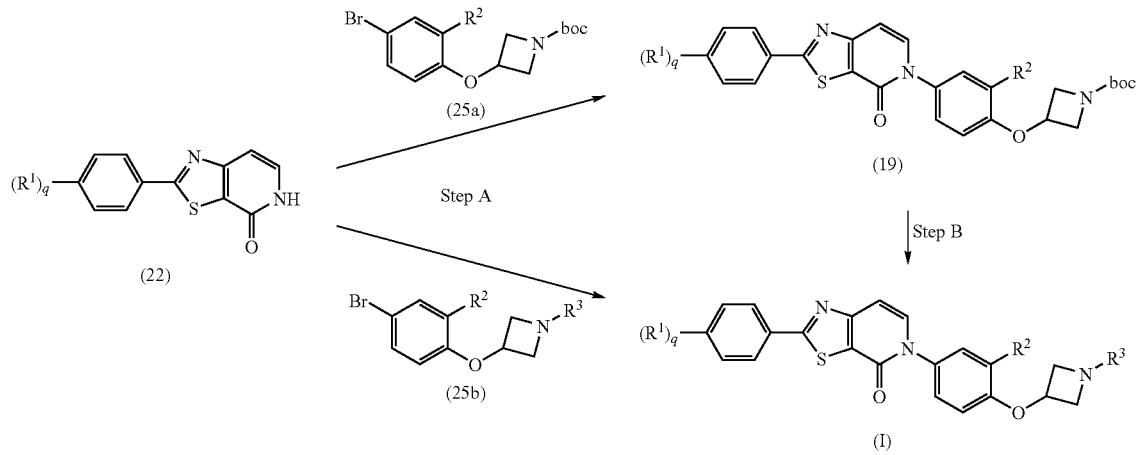

Depicted in Scheme 6 is yet another route for obtaining compounds of formula (I) utilizing a phenyl thiazolo-pyridinone of formula (22).

In Scheme 6, Step A, a phenyl thiazolo-pyridinone of formula (22) is coupled with a phenyl bromide of formula (25a)

*and activation*. Mol Pharmacol 58, 217-225. For GTPgammaS functional assay, see for example, Gao, X., et al., 2004. *Europium-labeled melanin-concentrating hormone analogues: ligands for measuring binding to melanin-concentrating hormone receptors* 1 *and* 2. Anal Biochem 328, 187-195.

All ligands, radioligands, solvents and reagents useful in these assays are readily available from commercial sources or can be readily prepared by those skilled in the art. $^{125}$I-MCH binding and functional GTPγ$^{35}$S binding assays employing membranes isolated from AV-12 cells transected with the human MCHR1 (Swiss-Prot Accession number Q99705) were used to demonstrate the effectiveness of compounds disclosed herein as MCHR1 antagonists. Binding of compounds to MCHR1 is assessed in a competitive binding assay employing $^{125}$I-MCH, compound of the invention, and clone 43 membranes using scintillation proximity techniques. $IC_{50}$ values (defined as the concentration of test compound required to reduce specific binding of $^{125}$I-MCH by 50%) are determined by fitting the concentration-response data to a 4-parameter model (max response, min response, Hill coefficient, $IC_{50}$) using a spreadsheet. $K_i$ values are calculated from $IC_{50}$ values using the Cheng-Prusoff approximation as described by Cheng et al. (*Biochem. Pharmacol.*, 22: 3099-3108 (1973). Exemplified compounds show a Ki of <1 µM in the binding assay disclosed herein. Specifically, the compound of Example 37 exhibits an average MCHR1 Ki of about 4 nM. Therefore, compounds of the invention are effective as potent MCHR1 antagonists.

Functional antagonism of MCH activity is assessed by measuring the ability of a test compound to inhibit MCH-stimulated binding of GTPγ$^{35}$S to membranes isolated from AV-12 cells expressing the human MCHR1 using a scintillation proximity assay. $IC_{50}$ values (defined as the concentration of test compound required to reduce MCH-stimulated GTPγ$^{35}$S binding by 50%) are determined by fitting the concentration-response data to a 4-parameter model (max response, min response, Hill coefficient, $IC_{50}$) using a spreadsheet. After verifying competitive antagonism by Schild analysis, $K_b$ values are calculated from the $IC_{50}$ values for each antagonist and the $EC_{50}$ for MCH (determined independently) using a modification of the Cheng-Prusoff approximation as described by Leff and Dougal (*Trends Pharmacol. Sci.* (1993) 14: 110-112). Exemplified compounds show $K_b$ values of <1 µM in the functional assay disclosed herein. Specifically, the compound of Example 28 shows a MCHR1 Kb value of about 6 nM. Thus, compounds of the invention are effective as potent MCHR1 antagonists.

To demonstrate in vivo efficacy, compounds of the invention are administered by oral gavage to diet-induced obese male Long-Evans rats (Harlan, Ind.) weighing 450-500 g. Animals are housed individually in a temperature regulated room (24° C.) with a reverse 12 hour light/dark cycle (dark 10:00/22:00). Water and food (Teklad 95217, Harlan, Wis.) were available ad libitum. Compounds are administered orally in a vehicle that consists of 10% acacia and 0.15% saccharin in water once a day before onset of the dark period for 3 days. Food intake and body weight are measured daily for the 3 day period. The compound of Example 29 produces an average body weight reduction of about 7 grams at a dose of 10 mg/Kg when compared to vehicle control. The results show that compounds of the invention are useful in treating obesity.

As antagonists of the MCHR1 binding, a compound of the present invention is useful in treating conditions in human and non-human (especially companion) animals in which the MCHR1 receptor has been demonstrated to play a role or diseases related to the effect of MCH. The diseases, disorders or conditions for which compounds of the present invention are useful in treating or preventing include disease disclosed herein and in PCT application WO 2007/066174. The compounds of the invention may also be used in combination with other approved therapeutic agents for treating, preventing and/or ameliorating obesity and related diseases. In this format, the compounds of the present invention enhance the positive effects of such approved combination treatments while minimizing the side effects due to the potential requirement of lower doses of such combination compounds. Such combination therapies may be delivered individually or in a combined formulation. Examples of compounds useful in combination with a compound of formula I or II include weight loss agents (Meridia™, Xenical™) cholesterol lowering agents (such as for example, lovastatin, simvastatin pravastatin, fluvastatin, and atorvastatin), glucose level control or modulating agents, cannabinoid CB-1 antagonist compounds (such as for example rimonanbant) and the like.

In treating non-human, non-companion animals, the compounds of the present invention are useful for reducing weight gain and/or improving the feed utilization efficiency and/or increasing lean body mass.

The compound of formula I or II is preferably formulated in a unit dosage form prior to administration. Therefore, yet another embodiment of the present invention is a pharmaceutical formulation comprising a compound of formula I or II and a pharmaceutical carrier.

The present pharmaceutical formulations are prepared by known procedures using well-known and readily available ingredients. In making the formulations of the present invention, the active ingredient (formula I or II compound) will usually be mixed with a carrier, or diluted by a carrier, or enclosed within a carrier which may be in the form of a liquid, tablet, capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

One of skill in the art is aware of methods, reagents and conditions for preparing various standard formulations or can assess such information without undue experimentation. The compositions of the invention may be formulated so as to provide quick, sustained or delayed release of the active ingredient after administration to the patient.

The specific dose administered is determined by the particular circumstances surrounding each situation. These circumstances include, the route of administration, the prior medical history of the patient, the pathological condition or symptom being treated, the severity of the condition/symptom being treated, and the age and sex of the recipient. However, it will be understood that the therapeutic dosage administered will be determined by the physician in the light of the relevant circumstances, or by the veterinarian for non-human recipients.

Generally, an effective minimum daily dose of a compound of formula I or II is about 0.1 mg to about 0.5 mg per kilogram. An effective maximum dose is about 1 mg to about 5 mg per kilogram. The exact dose appropriate for a particular recipient is a determination to be made by the treating physician based on the particular circumstances of the patient. The appropriate dose may also be determined, in accordance with the standard practice in the medical arts of "dose titrating" the recipient; that is, initially administering a low dose of the compound, and gradually increasing the dose until the desired therapeutic effect is observed.

The compounds may be administered by a variety of routes including the oral, rectal, transdermal, subcutaneous, topical, intravenous, intramuscular or intranasal routes. A preferred route of administration is oral.

Examples

Without further elaboration, it is believed that one skilled in the art can, using the preceding description, practice the present invention to its fullest extent. The following preparations and examples are provided to describe the invention in further detail. They are intended to illustrate and not to limit the invention in any way whatsoever. The reagents and starting materials are readily available to, or may be readily synthesized by, one of ordinary skill in the art. Those skilled in the art will promptly recognize appropriate variations from the procedures described in the examples. The names of the compounds of the present invention are provided by ChemDraw Ultra® version 7.0.1.

Preparation 1

[2-(4-Chloro-phenyl)-thiazol-4-yl]acetic acid ethyl ester

Dissolve 4-chlorothiobenzamide (74.0 g, 431.1 mmol) in EtOH (470 mL) and treat with ethyl-4-chloroacetoacetate (58.0 mL, 70.1 g, 426.0 mmol). Stir the resulting solution mechanically at reflux for 2 h. Cool to room temperature, add water (1000 mL), and extract with $Et_2O$ (2000 mL, then 2×500 mL). Combine the organic solutions and wash with brine (950 mL). Concentrate in vacuo to give an oil that solidifies upon standing (121.8 g). Recrystallize the crude material from isopropanol/water to give the title compound (107.3 g, 89% yield). ES/MS m/z ($^{35}Cl$) 282.1 [M+1]$^+$.

Preparation 2

2-[2-(4-Chloro-phenyl)-thiazol-4-yl]ethanol

Dissolve [2-(4-chloro-phenyl)-thiazol-4-yl]-acetic acid ethyl ester (107.4 g, 381.2 mmol) in THF (800 mL) and cool to 0-5° C. Slowly add DIBAL (1.0 M in THF, 800 mL, 800 mmol) over approximately 3.5 h keeping the temperature<5° C. After the addition is complete warm the resulting solution to room temperature and stir mechanically overnight. Cool the solution to 0-5° C. and slowly add additional DIBAL (150 mL) keeping the temperature<5° C. Stir at room temperature for 2.5 h, then cool to 0-5° C. and slowly quench over 5 h with aqueous saturated Rochelle's salt (2900 mL) keeping the temperature<10° C. Extract the mixture with EtOAc (2×3300 mL). Combine the organic solutions and concentrate in vacuo to give an oil (112.9 g). Dissolve the oil in toluene (600 mL) and concentrate in vacuo, then repeat. Dry the residue in vacuo for 6 h to give a residue weighing 107.4 g (110%). ES/MS m/z ($^{35}Cl$) 240.1 [M+1]$^+$.

Preparation 3

2-(4-Chloro-phenyl)-4-(2-hydroxy-ethyl)-thiazole-5-carboxylic acid

Dissolve 2-[2-(4-chloro-phenyl)-thiazol-4-yl]-ethanol (107 g gross, 91 g net, 380 mmol) in THF (1210 mL) and cool to about −75° C. Evacuate the chilled solution under vacuum and fill with nitrogen three times. Slowly add n-BuLi (1.6 M in hexanes, 530 mL, 848 mmol) over approximately 4 h, keeping the temperature<−70° C. Slowly add the red-purple solution via cannula over 3.5 h to a flask containing −75° C. THF that has been saturated with $CO_2$ gas (approximately 390 g) keeping the temperature<−60° C. Charge the resulting brown slurry with additional $CO_2$ gas (approximately 355 g) and then allow the slurry to come to room temperature while stirring mechanically overnight. Quench the reaction with 1 N HCl (3000 mL), cool to 16° C., and collect the precipitate by filtration. Rinse the solid with hexanes (1400 mL) and dry under vacuum to give 81.3 g (75%) of the title compound. ES/MS m/z ($^{35}Cl$) 284.0 [M+1]$^+$.

Preparation 4

2-(4-Chloro-phenyl)-6,7-dihydro-pyrano[4,3-d]thiazol-4-one

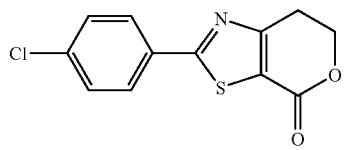

Mix 2-(4-chloro-phenyl)-4-(2-hydroxy-ethyl)-thiazole-5-carboxylic acid (81.2 g, 286.2 mmol) with p-TsOH monohydrate (32.0 g, 168.2 mmol) and toluene (1200 mL). Heat the slurry to reflux during which time the solids dissolve. Stir the resulting tan solution mechanically for 2 h, using a Dean-Stark trap to collect water (21 mL). Cool the solution to room temperature and add saturated aqueous $NaHCO_3$ (1700 mL) and EtOAc (1700 mL). Separate the organic solution, then extract the aqueous layer with EtOAc (2×1700 mL). Combine the organic solutions, wash with brine (1700 mL), and concentrate in vacuo to give a solid. Mix the solid with $CH_2Cl_2$ (500 mL) and concentrate in vacuo and repeat two times to give 60.1 g (79%) of the title compound. ES/MS m/z ($^{35}Cl$) 266.0 [M+1]$^+$.

Preparation 5

2-(4-Chloro-phenyl)-4-(2-hydroxy-ethyl)-thiazole-5-carboxylic acid methyl ester

Dissolve 2-(4-chloro-phenyl)-6,7-dihydro-pyrano[4,3-d]thiazol-4-one (500 g, 1882 mmol) in MeOH (5 L) and add concentrated sulfuric acid (31 mL). Stir the solution at 55° C. for 15 h, then warm to 66° C. and continue stirring for an additional 4.5 h. Cool the solution to 45° C. and concentrate in vacuo to one half of the volume. Continue to cool the slurry to 20° C. Isolate the precipitate by filtration and wash the solid with cold MeOH. Dry the solid (420.5 g) under vacuum overnight. Concentrate the filtrate to about 600 mL, filter, and wash with cold MeOH to obtain more solid (40.7 g). Purify the crude materials by flash chromatography, using 10% EtOAc/$CH_2Cl_2$ as eluent, to give a total of (442 g, 80%) of the title compound. $^1H$ NMR (400 MHz, $CDCl_3$): δ 7.88 (dt, J=8.8, 4.7 Hz, 2H), 7.43 (dt, J=8.7, 4.3 Hz, 2H), 4.05 (t, J=5.6 Hz, 2H), 3.90 (s, 3H), 3.43 (t, J=5.6 Hz, 2H), 3.32 (bs, 1H).

Preparation 6

2-(4-Chloro-phenyl)-4-(2-oxo-ethyl)-thiazole-5-carboxylic acid methyl ester

Dissolve 2-(4-chloro-phenyl)-4-(2-hydroxy-ethyl)-thiazole-5-carboxylic acid methyl ester (100 g, 336 mmol) in $CH_2Cl_2$ (2 L) and treat with potassium bromide (4.0 g, 33.6 mmol) and TEMPO (1.1 g, 7.0 mmol). Cool the solution to −10° C. and add a solution of sodium hypochlorite (1 L, 0.25 M in water) and aqueous sodium bicarbonate (1 L, 1.4 M). Stir the resulting slurry at 0° C. for 15 min and then dilute with water (3.2 L) and $CH_2Cl_2$ (1.3 L). Remove the organic solution and extract the aqueous phase with $CH_2Cl_2$ (1.3 L). Combine the organic solutions and wash with brine (1.3 L), then dry, filter, and concentrate to give (91.5 g, 92%) of the title compound. $^1$H NMR (400 MHz, $CDCl_3$): δ 9.86 (t, J=1.5 Hz, 1H), 7.90 (dt, J=8.4, 4.4 Hz, 2H), 7.43 (dt, J=8.6, 4.4 Hz, 2H), 4.32 (d, J=1.8 Hz, 2H), 3.89 (s, 3H).

Preparation 7

2-(4-Chloro-phenyl)-4-(2,2-dimethoxy-ethyl)-thiazole-5-carboxylic acid methyl ester Mix 2-(4-chloro-phenyl)-4-(2-oxo-ethyl)-thiazole-5-carboxylic acid methyl ester (96.4 g, 308 mmol), Dowex™ 50×8 ion exchange resin (33.3 g), and trimethyl orthoformate (147 mL) in MeOH (670 mL). Stir the slurry overnight at room temperature. Filter through a plug of diatomaceous earth and rinse with MeOH (3×300 mL). Stir the filtrate at 0° C. for 2 h and then concentrate to a volume of approximately 250 mL. Collect the solid by filtration, rinse with cold MeOH, and dry overnight at room temperature to obtain 88.2 g (84%) of the titled compound. ES/MS m/z ($^{35}$Cl) 342.0 [M+1]$^+$.

Preparation 8

2-(4-Chloro-phenyl)-4-(2,2-dimethoxy-ethyl)-thiazole-5-carboxylic acid

Mix 2-(4-chloro-phenyl)-4-(2,2-dimethoxy-ethyl)-thiazole-5-carboxylic acid methyl ester (3.6 g, 10.5 mmol) in EtOH (40 mL) and then add 2 M NaOH (6.8 mL). Stir the slurry mechanically overnight and then concentrate in vacuo. Dissolve the solid in water (40 mL), cool to 0° C., and adjust the pH to 5-6 with 1 N HCl (13 mL). Stir the slurry for 15 min, collect the precipitate, and wash the solid with water (4×20 mL). Dry the solid in a vacuum oven overnight to give 3.3 g (96%) of the title compound. ES/MS m/z ($^{35}$Cl) 326.0 [M−1]$^−$.

Preparation 9

3-(2-Methoxy-4-nitro-phenoxy)-azetidine-1-carboxylic acid tent-butyl ester

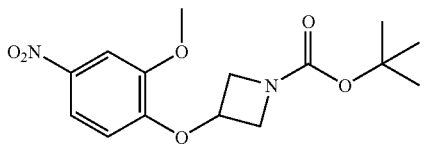

Dissolve 1-fluoro-2-methoxy-4-nitro-benzene (118 g, 689 mmol) and 3-hydroxy-azetidine-1-carboxylic acid tert-butyl ester (125 g, 724 mmol) in THF (800 mL) and cool to 0° C. under nitrogen. To the above solution, add dropwise a 1 M THF solution of tert-BuOK (1 L). After the addition is complete, stir the dark brown solution for 30 min at 0° C. and then dilute with water (1 L) over a 10 min period. Stir the mixture for 5 min, then extract with tert-butyl methyl ether (2×). Combine the organic solutions and wash with brine (2×700 mL), then dry and concentrate. Dry the solid in vacuo at 45° C. for 20 h to obtain 216 g (95%) of the title compound as a yellow solid. $^1$H NMR (300 MHz, $CDCl_3$) δ: 6.47 (d, 1H, J=8.5), 6.30 (d, 1H, J=2.6), 6.17 (dd, 1H, J=2.4, 8.5), 4.76 (m, 1H), 4.18 (m, 2H), 4.04 (m, 2H), 3.80 (s, 3H), 1.42 (s, 9H).

Prepare the nitro compounds in the table below, Preparations 10 to 13, by essentially following the procedure as described in Preparation 9.

| Prep | Product (Chemical Name) | NMR |
|---|---|---|
| 10 | 3-(2-Fluoro-4-nitro-phenoxy)-azetidine-1-carboxylic acid tert-butyl ester | $^1$H NMR (300 MHz, $CD_3OD$) δ: 8.05 (m, 2H), 7.01 (m, 1H), 5.15 (m, 1H), 4.38 (dd, 2H, J = 2.7, 9.5), 3.96 (bd, 2H), 1.43 (s, 9H). |
| 11 | 3-(2-Cyano-4-nitro-phenoxy)-azetidine-1-carboxylic acid tert-butyl ester | $^1$H NMR (300 MHz, $CD_3OD$) δ: 8.6 (d, 1H, J = 2.7), 8.45 (dd, 1H, J = 6.5, 9.2), 7.08 (d, 1H, J = 9.2), 5.24 (m, 1H), 4.42 (dd, 2H, J = 2.5, 9.5), 4.0 (bd, 2H), 1.43 (s, 9H). |
| 12 | 3-(2-Chloro-4-nitro-phenoxy)-azetidine-1-carboxylic acid tert-butyl ester | $^1$H NMR (300 MHz, $CD_3OD$) δ: 8.31 (d, 1H, J = 2.8), 8.16 (dd, 1H, J = 6.2, 9.1), 6.96 (d, 1H, J = 8.9), 5.16 (m, 1H), 4.39 (dd, 2H, J = 2.9, 9.3), 3.96 (bd, 2H), 1.43 (s, 9H). |
| 13 | 3-(4-Nitro-phenoxy)-azetidine-1-carboxylic acid tert-butyl ester | $^1$H NMR (300 MHz, $CD_3OD$) δ: 8.2 (d, 2H, J = 9.2), 6.96 (d, 2H, J = 9.3), 5.08 (m, 1H), 4.36 (dd, 2H, J = 2.4, 9.4), 3.91 (dd, 2H, J = 6.6, 9.7), 1.42 (s, 9H) |

Preparation 14

3-(4-Amino-2-methoxy-phenoxy)-azetidine-1-carboxylic acid tert-butyl ester

Dissolve 3-(2-methoxy-4-nitro-phenoxy)-azetidine-1-carboxylic acid tert-butyl ester (210 g, 639 mmol) in THF (630 mL) and transfer with MeOH (1680 mL) to a stainless steel tank containing 10% palladium on carbon pre-wet with toluene. Hydrogenate the mixture on a Parr shaker for 2.5 h. Remove the catalyst by filtration through diatomaceous earth and rinse the solids with MeOH. Concentrate the filtrate in vacuo, and then co-evaporate the residue three times with heptane (500 mL each time) to obtain 190 g (99%) of the title compound as a tan solid which is used immediately in the next reaction. $^1$H NMR (300 MHz, $CDCl_3$) δ: 6.48 (d, 1H, J=8.5), 6.30 (d, 1H, J=2.6), 6.17 (dd, 1H, J=2.4, 8.5), 4.77 (m, 1H), 4.19 (m, 2H), 4.04 (m, 2H), 3.81 (s, 3H), 3.59 (br s, 2H), 1.42 (s, 9H).

Prepare the aniline compounds in the table below, Preparations 15 and 16, by essentially following the procedure as described in Preparation 14.

| Prep | Product (Chemical Name) | NMR |
|---|---|---|
| 15 | 3-(4-Amino-2-fluoro-phenoxy)-azetidine-1-carboxylic acid tert-butyl ester | $^1$H NMR (300 MHz, CDCl$_3$) δ: 6.56 (t, 1H, J = 8.8), 6.42 (dd, 1H, J = 10.1, 12.8), 6.30 (m, 1H), 4.74 (m, 1H), 4.0 (dd, 2H, J = 6.3, 10.4), 3.53 (bs, 2H), 1.41 (s, 9H). |
| 16 | 3-(4-Amino-phenoxy)-azetidine-1-carboxylic acid tert-butyl ester | $^1$H NMR (300 MHz, CDCl$_3$) δ: 6.57 (dd, 4H, J = 9.3, 18), 4.74 (m, 1H), 4.2 (dd, 2H, J = 3.5, 10.2), 3.94 (dd, 2H, J = 5.9, 10.2), 3.43 (bs, 2H), 1.41 (s, 9H) |

Preparation 17

3-(4-Amino-2-cyano-phenoxy)-azetidine-1-carboxylic acid tent-butyl ester

Dissolve 3-(2-cyano-4-nitro-phenoxy)-azetidine-1-carboxylic acid tert-butyl ester (1 g, 3.13 mmol) in dry EtOH (12.53 mL). Add saturated NH$_4$Cl solution (3.77 mL, 17.28 mmol) and indium (2.2 g, 19.15 mmol). Heat to reflux for one hour. Quench the mixture with water (50 mL) and filter through diatomaceous earth. Neutralize the mixture with pH=7 buffer and extract with CH$_2$Cl$_2$ (2×20 mL). Combine the organic layers and wash with water (30 mL). Dry, filter, and concentrate the organic solution. Purify the crude material by flash chromatography, using 0-50% EtOAc/hexanes as eluent, to provide 660 mg (72%) of the desired product. $^1$H NMR (300 MHz, CDCl$_3$) δ: 6.85 (d, 1H, J=3), 6.78 (dd, 1H, J=6.1, 8.7), 6.44 (d, 1H, J=9), 4.82 (m, 1H), 4.24 (dd, 2H, J=3.0, 9.6), 4.02 (dd, 2H, J=5.8, 9.8), 3.53 (bs, 2H), 1.42 (s, 9H).

Prepare the aniline compound in the table below by essentially following the procedure as described in Preparation 17.

| Prep | Product (Chemical Name) | NMR |
|---|---|---|
| 18 | 3-(4-Amino-2-chloro-phenoxy)-azetidine-1-carboxylic acid tert-butyl ester | $^1$H NMR (300 MHz, CDCl$_3$) δ: 6.72 (s, 1H), 6.46 (s, 2H), 4.76 (m, 1H), 4.20 (dd, 2H, J = 4.4, 10.4), 4.02 (dd, 2H, J = 6.2, 10.6), 3.48 (bs, 2H), 1.42 (s, 9H). |

Preparation 19

3-(4-{[2-(4-Chloro-phenyl)-4-(2,2-dimethoxy-ethyl)-thiazole-5-carbonyl]-amino}-2-methoxy-phenoxy)-azetidine-1-carboxylic acid tert-butyl ester Dissolve 2-(4-chloro-phenyl)-4-(2,2-dimethoxy-ethyl)-thiazole-5-carboxylic acid (147 g, 448 mmol), 3-(4-amino-2-methoxy-phenoxy)-azetidine-1-carboxylic acid tert-butyl ester (120 g, 402 mmol), and 1-hydroxybenzotriazole hydrate (75 g, 490 mmol) in THF (1.2 L) and cool to about 10° C. under a nitrogen atmosphere Treat the above solution with diisopropylethylamine (117 mL, 673 mmol) dropwise over 2 min while keeping the temperature between 10-15° C. Add 1-(3-dimethylaminopropyl)-3-ethylcarbodiimide hydrochloride (93 g, 489 mmol) to the solution and stir at room temperature for 19 h. Cool the solution to 0° C. and dilute with water (1.2 L). Collect the precipitate by filtration and triturate with water (5×700 mL). Dry the tan solid for 3 days at 50° C. under vacuum to obtain 219 g (90%) of the title compound. $^1$H NMR (300 MHz, CDCl$_3$) δ: 10.03 (s, 1H), 7.90 (m, 2H), 7.66 (d, 1H, J=2.4), 7.42 (m, 2H), 6.88 (dd, 1H, J=2.4, 8.6), 6.57 (d, 1H, J=8.6), 4.86 (m, 1H), 4.84 (t, 1H, J=5.7), 4.26 (dd, 2H, J=6.7, 10.6), 4.08 (dd, 2H, J=4.3, 10.6), 3.90 (s, 3H), 3.53 (s, 6H), 3.37 (d, 2H, J=5.5), 1.43 (s, 9H).

Preparation 20

3-(4-{[2-(4-Chloro-phenyl)-4-(2-hydroxy-ethyl)-thiazole-5-carbonyl]-amino}-2-methoxy-phenoxy)-azetidine-1-carboxylic acid tent-butyl ester

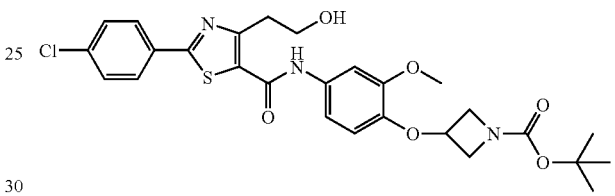

Dissolve 3-(4-amino-2-methoxy-phenoxy)-azetidine-1-carboxylic acid tert-butyl ester (9.1 g, 30.9 mmol) in toluene (100 mL) at room temperature and treat with trimethylaluminum (22.0 mL, 2.0 M in toluene). Stir the dark red solution at room temperature for one hour and add solid 2-(4-chloro-phenyl)-6,7-dihydro-pyrano[4,3-d]thiazol-4-one (7.97 g, 30.0 mmol). Warm the solution to 50° C. and stir for 2 h. Cool to room temperature and slowly quench with saturated Rochelle's salt solution (5 mL). After the bubbling subsides add additional Rochelle's salt solution (30 mL) and stir vigorously for 2 h. Separate the organic phase and extract the aqueous phase with CH$_2$Cl$_2$ (2×50 mL). Combine the organic portions and wash with saturated Rochelle's salt solution (2×25 mL) and brine (25 mL). Dry, filter, and concentrate the organic solution. Purify the crude material by flash chromatography, using 5% MeOH (2M NH$_3$)/CH$_2$Cl$_2$ as eluent, to give an orange solid. Further purify the material by trituration with 1:1 CH$_2$Cl$_2$:diethyl ether, followed by filtration to give 12.77 g, (76%) of the title compound as a white solid. ES/MS m/z ($^{35}$Cl) 558.2 [M−1]$^-$.

Prepare the alcohol-amide compounds in the table below, Preparations 21 to 25, by essentially following the procedure as described in Preparation 20.

| Prep | Product (Chemical Name) | ES/MS m/z |
|---|---|---|
| 21 | 3-(4-{[2-(4-Chloro-phenyl)-4-(2-hydroxy-ethyl)-thiazole-5-carbonyl]-amino}-phenoxy)-azetidine-1-carboxylic acid tert-butyl ester | ($^{35}$Cl) 530.2 [M + 1]$^+$ |
| 22 | 3-(4-{[2-(4-Chloro-phenyl)-4-(2-hydroxy-ethyl)-thiazole-5-carbonyl]-amino}-2-fluoro-phenoxy)-azetidine-1-carboxylic acid tert-butyl ester | ($^{35}$Cl) 548 [M + 1]$^+$ |

| Prep | Product (Chemical Name) | ES/MS m/z |
|---|---|---|
| 23 | 3-(2-Chloro-4-{[2-(4-chloro-phenyl)-4-(2-hydroxy-ethyl)-thiazole-5-carbonyl]-amino}-phenoxy)-azetidine-1-carboxylic acid tert-butyl ester | ($^{35}$Cl) 564 [M + 1]$^+$ |
| 24 | 3-(4-{[2-(4-Chloro-phenyl)-4-(2-hydroxy-ethyl)-thiazole-5-carbonyl]-amino}-2-cyano-phenoxy)-azetidine-1-carboxylic acid tert-butyl ester | ($^{35}$Cl) 553 [M − 1]$^−$ |
| 25 | 3-(4-{[2-(4-Fluoro-phenyl)-4-(2-hydroxy-ethyl)-thiazole-5-carbonyl]-amino}-2-methoxy-phenoxy)-azetidine-1-carboxylic acid tert-butyl ester | 544.8 (M + 1)$^+$ |

Preparation 26

3-{4-[2-(4-Chloro-phenyl)-4-oxo-6,7-dihydro-4H-thiazolo[5,4-c]pyridin-5-yl]-2-methoxy-phenoxy}-azetidine-1-carboxylic acid tert-butyl ester

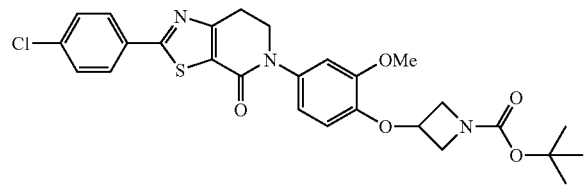

Dissolve 3-(4-{[2-(4-chloro-phenyl)-4-(2-hydroxy-ethyl)-thiazole-5-carbonyl]-amino}-2-methoxy-phenoxy)-azetidine-1-carboxylic acid tert-butyl ester (9.1 g, 30.9 mmol) in THF (100 mL) at room temperature and treat with tri-n-butylphosphine (6.2 mL, 24.8 mmol) and diisopropyl azodicarboxylate (5.0 g, 24.7 mmol). Stir the solution at 50° C. for 5 h, then cool to room temperature and concentrate in vacuo to ¼ volume. Dilute the yellow mixture with diethyl ether (100 mL) and collect the light yellow powder by filtration, washing with additional diethyl ether (50 mL). Dry the solid in vacuo to obtain 9.7 g (79%) of the title compound as a light yellow solid. ES/MS m/z ($^{35}$Cl) 542.2 [M+1]$^+$, 564.2 [M+Na]$^+$.

Prepare the lactam compounds in the table below, Preparations 27 to 31, by essentially following the procedure as described in Preparation 26.

| Prep | Product (Chemical Name) | ES/MS m/z |
|---|---|---|
| 27 | 3-{4-[2-(4-Chloro-phenyl)-4-oxo-6,7-dihydro-4H-thiazolo[5,4-c]pyridin-5-yl]-2-cyano-phenoxy}-azetidine-1-carboxylic acid tert-butyl ester | ($^{35}$Cl) 537 [M + 1]$^+$ |
| 28 | 3-{2-Chloro-4-[2-(4-chloro-phenyl)-4-oxo-6,7-dihydro-4H-thiazolo[5,4-c]pyridin-5-yl]-phenoxy}-azetidine-1-carboxylic acid tert-butyl ester | ($^{35}$Cl) 546 [M + 1]$^+$ |
| 29 | 3-{4-[2-(4-Chloro-phenyl)-4-oxo-6,7-dihydro-4H-thiazolo[5,4-c]pyridin-5-yl]-2-fluoro-phenoxy}-azetidine-1-carboxylic acid tert-butyl ester | ($^{35}$Cl) 530 [M + 1]$^+$ |
| 30 | 3-{4-[2-(4-Chloro-phenyl)-4-oxo-6,7-dihydro-4H-thiazolo[5,4-c]pyridin-5-yl]-phenoxy}-azetidine-1-carboxylic acid tert-butyl ester | ($^{35}$Cl) 512 [M + 1]$^+$ |
| 31 | 3-{4-[2-(4-Fluoro-phenyl)-4-oxo-6,7-dihydro-4H-thiazolo[5,4-c]pyridin-5-yl]-2-methoxy-phenoxy}-azetidine-1-carboxylic acid tert-butyl ester | 470 [M − 56 (t-butyl)]$^+$1 |

Example 1

5-[4-(Azetidin-3-yloxy)-3-methoxy-phenyl]-2-(4-chloro-phenyl)-5H-thiazolo[5,4-c]pyridin-4-one

Dissolve 3-(4-{[2-(4-chloro-phenyl)-4-(2,2-dimethoxy-ethyl)-thiazole-5-carbonyl]-amino}-2-methoxy-phenoxy)-azetidine-1-carboxylic acid tert-butyl ester (18.9 g, 31.28 mmol) and p-toluenesulfonic acid monohydrate (19.7 g, 103.56 mmol) in dry toluene (460 mL) and stir mechanically at 95° C. overnight. Cool the reaction mixture and add 1 N NaOH. Stir the mixture vigorously at room temperature for one hour. Extract the aqueous layer with CH$_2$Cl$_2$ (2×700 mL). Combine the organic portions, wash with brine (700 mL), dry over MgSO$_4$, and filter. Concentrate the filtrate in vacuo to give 13.0 g (85%) of the title compound. ES/MS m/z ($^{35}$Cl) 440.0 [M+1]$^+$.

Example 1a

5-[4-(Azetidin-3-yloxy)-3-methoxy-phenyl]-2-(4-chloro-phenyl)-5H-thiazolo[5,4-c]pyridin-4-one, hydrochloride salt Mix 3-(4-{[2-(4-chloro-phenyl)-4-(2,2-dimethoxy-ethyl)-thiazole-5-carbonyl]-amino}-2-methoxy-phenoxy)-azetidine-1-carboxylic acid tert-butyl ester (208 g, 344 mmol) in EtOH (2.2 L) and treat with concentrated HCl (208 mL). Heat the mixture to reflux for one hour and then cool to 0° C. Collect the solid by filtration and rinse with ice-cold Et$_2$O (4×500 mL). Dry the solid under vacuum at 55° C. for 2 days to give 159 g (97%) of the title compound as an off-white solid. $^1$H NMR (300 MHz, DMSO-d6) δ: 9.37 (s, 2H), 8.15 (m, 2H), 7.75 (d, 1H, J=7.6), 7.66 (m, 2H), 7.22 (d, 1H, J=7.5), 7.05 (d, 1H, J=7.3), 7.01 (dd, 1H, J=2.5, 8.7), 6.92 (d, 1H, J=8.6), 5.09 (m, 1H), 4.45 (m, 2H), 4.04 (m, 2H), 3.82 (s, 3H).

Preparation 32

3-{4-[2-(4-Chloro-phenyl)-4-oxo-4H-thiazolo[5,4-c]pyridin-5-yl]-2-fluoro-phenoxy}-azetidine-1-carboxylic acid tert-butyl ester Dissolve 3-(4-{[2-(4-chloro-phenyl)-4-(2-hydroxy-ethyl)-thiazole-5-carbonyl]-amino}-2-fluoro-phenoxy)-azetidine-1-carboxylic acid tert-butyl ester (260 mg, 0.474 mmol) in dry DMSO (3.16 mL) followed by addition of triethylamine (0.125 mL, 0.901 mmol). Chill the mixture to 15° C. and add portion-wise sulfur trioxide pyridine complex (133 mg, 0.820 mmol). Stir for approximately 2 h. (Note: additional Pyr*SO$_3$ may be needed until starting material is consumed). Quench the mixture with water (10 mL) and extract with CH$_2$Cl$_2$ (2×25 mL). Dry, filter, and concentrate to dryness.

Redissolve the crude material in CH$_2$Cl$_2$ (1.9 mL) and add TFA (0.558 mL, 7.38 mmol) and stir until the reaction is complete by TLC (1:1 EtOAc/hexanes). Quench the mixture with water (10 mL) and 5 N NaOH solution to pH=8-10. Extract aqueous layer with CH$_2$Cl$_2$ (2×25 mL). Dry, filter, and concentrate to a white solid. Triturate with Et$_2$O to give 46 mg (22%) of a tan solid. ES/MS m/z ($^{35}$Cl) 428.0 [M+1]$^+$.

Example 2

2-(4-Chloro-phenyl)-5-[4-(1-cyclobutyl-azetidin-3-yloxy)-3-methoxy-phenyl]-5H-thiazolo[5,4-c]pyridin-4-one, hydrochloride salt

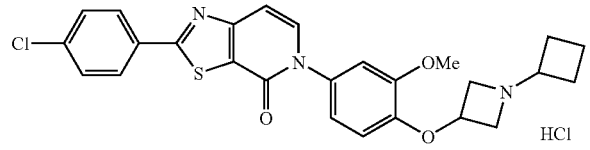

Method 1: Dissolve 3-(4-{[2-(4-chloro-phenyl)-4-(2,2-dimethoxy-ethyl)-thiazole-5-carbonyl]-amino}-2-methoxy-phenoxy)-azetidine-1-carboxylic acid tert-butyl ester (18.9 g, 31.28 mmol) and p-toluenesulfonic acid monohydrate (19.7 g, 103.56 mmol) in dry toluene (460 mL) and stir mechanically at 95° C. overnight. Cool the reaction mixture and add 1 N NaOH. Stir the mixture vigorously at room temperature for one hour. Extract the aqueous layer with CH$_2$Cl$_2$ (2×700 mL). Combine the organic portions, wash with brine (700 mL), dry over MgSO$_4$, and filter. Concentrate the filtrate in vacuo to give 13.0 g (85%) of 5-[4-(azetidin-3-yloxy)-3-methoxy-phenyl]-2-(4-chloro-phenyl)-5H-thiazolo[5,4-c]pyridin-4-one. ES/MS m/z 440.0 ($^{35}$Cl) [M+1]$^+$.

Dissolve 5-[4-(azetidin-3-yloxy)-3-methoxy-phenyl]-2-(4-chloro-phenyl)-5H-thiazolo[5,4-c]pyridin-4-one (300 mg, 0.680 mmol) and cyclobutanone (76 µL, 1.02 mmol) in dry 1,2-dichloroethane (6.66 mL). Mix well and add sodium triacetoxyborohydride (500 mg, 2.26 mmol). Stir overnight at room temperature. Add 1 N NaOH solution and extract with CH$_2$Cl$_2$ (2×10 mL). Combine the organic portions and wash with water (2×5 mL). Dry with Na$_2$SO$_4$, filter, and concentrate in vacuo. Purify the crude material by silica gel chromatography using a gradient of 0-10% 2 N NH$_3$/MeOH in CH$_2$Cl$_2$. Collect the desired fractions and remove solvent via reduced pressure. Re-dissolve material in CHCl$_3$ and add 1 N HCl solution (about 300 µL). Remove the solvent via reduced pressure and dry in vacuo at room temperature overnight to give 161 mg (44%) of the title compound. ES/MS m/z 494.0 ($^{35}$Cl) [M+1]$^+$.

Method 2:

Dissolve 3-{4-[2-(4-chloro-phenyl)-4-oxo-4H-thiazolo[5,4-c]pyridin-5-yl]-2-methoxy-phenoxy}-azetidine-1-carboxylic acid tert-butyl ester (15.6 g, 28.9 mmol) in CHCl$_3$ (156 mL) and MeOH (156 mL). Add concentrated aqueous HCl (6 mL, 79.2 mmol). Heat the resulting solution at 55-60° C. overnight. Cool the reaction to room temperature. Add cyclobutanone (12 g, 171.2 mmol) at 5-10° C. Then add portionwise sodium triacetoxyborohydride (43.6 g, 205.7 mmol). Stir the mixture at room temperature overnight. Quench the reaction slowly with a solution of Na$_2$CO$_3$ (210 mL) in water (300 mL) to bring the mixture to a pH=8. Add water (90 mL) and CHCl$_3$ (120 mL) and filter. Collect the filtrate and wash the organic layer with water (150 mL). Concentrate in vacuo to give a white solid 11.2 g (78%) of the title compound.

Example 3

2-(4-Chloro-phenyl)-5-[4-(1-cyclopropyl-azetidin-3-yloxy)-3-methoxy-phenyl]-5H-thiazolo[5,4-c]pyridin-4-one, hydrochloride salt Mix molecular sieves (100 mg, type 3A), 5-[4-(azetidin-3-yloxy)-3-methoxy-phenyl]-2-(4-chloro-phenyl)-5H-thiazolo[5,4-c]pyridin-4-one (1.00 g, 2.27 mmol), and [(1-ethoxycyclopropyl)oxy]trimethylsilane (688.3 µL, 3.41 mmol), and acetic acid (651.3 µL, 11.37 mmoles) in dry methanol (11 mL) and reflux the mixture for 3 h. Cool the reaction to room temperature, then add sodium cyanoborohydride (376 mg, 5.68 mmoles) and slowly warm to 40° C. for one hour. Cool the mixture and add 1 N NaOH solution, then extract the aqueous layer with CHCl$_3$ (3×25 mL). Dry the organic layer with Na$_2$SO$_4$, filter, and concentrate. Purify the crude material on silica gel chromatography using a gradient of 0-10% 2 N NH$_3$/MeOH in CHCl$_3$. Collect the desired fractions and remove the solvent via reduced pressure. Re-dissolve the resulting material in CHCl$_3$ and add 1 N HCl/Et$_2$O solution (2.27 mL). Remove the solvent and dry under vacuum to give 408 mg (35%) of the title compound. ES/MS m/z ($^{35}$Cl) 480.0 [M+1]$^+$.

Example 4

5-[4-(1-Acetyl-azetidin-3-yloxy)-3-methoxy-phenyl]-2-(4-chloro-phenyl)-5H-thiazolo[5,4-c]pyridin-4-one Dissolve 5-[4-(azetidin-3-yloxy)-3-methoxy-phenyl]-2-(4-chloro-phenyl)-5H-thiazolo[5,4-c]pyridin-4-one (75 mg, 0.171 mmol) and triethylamine (52.5 µL, 0.376 mmol) in dry CH$_2$Cl$_2$ (700 µL). Chill to 0° C. and add acetylchloride (13.4 µL, 0.188 mmol). Allow to warm to room temperature overnight. Add 1 N HCl solution and extract with CH$_2$Cl$_2$ (3×5 mL). Combine the organic portions and wash with water (2×5 mL). Dry the organic layer with Na$_2$SO$_4$, filter, and concentrate in vacuo. Purify the resulting residue on HPLC with 5 µm 30×75 mm XBridge C18 column; eluent: 34% water (with 10 mM NH$_4$HCO$_3$ added to pH=10/acetonitrile (isocratic) to give 39 mg, (48%). ES/MS m/z ($^{35}$Cl) 481.8 [M+1]$^+$.

Example 5

2-(4-Chloro-phenyl)-5-[3-methoxy-4-(1-methyl-azetidin-3-yloxy)-phenyl]-5H-thiazolo[5,4-c]pyridin-4-one

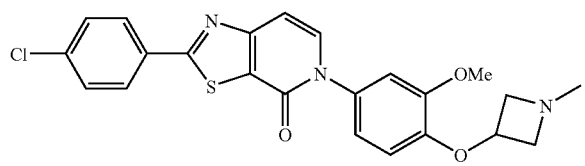

Cool a mixture of 5-[4-(azetidin-3-yloxy)-3-methoxy-phenyl]-2-(4-chloro-phenyl)-5H-thiazolo[5,4-c]pyridin-4-one, hydrochloride salt (20 g, 42.0 mmol) in methanol (600 mL) to 15° C. Add acetic acid (12.1 mL, 211.6 mmol) and sodium cyanoborohydride (7 g, 111 mmol). Add formaldehyde (10.2 mL, 136.45 mmol, as a solution in water to the thick mixture and stir for 15 h at room temperature. Cool the mixture to 5° C., add saturated aqueous $NaHCO_3$ (320 mL), and stir the mixture for one hour at room temperature. Extract the mixture with $CHCl_3$ (3×1 L). Combine the organic solutions and wash with brine, then dry, filter, and concentrate. Dissolve the residue in $CHCl_3$ (240 mL) and dilute with tert-butyl methyl ether (700 mL). Collect the precipitate by filtration and rinse the solids with additional tert-butyl methyl ether. Dry the solid under vacuum for 5 h at room temperature to obtain 5.4 g (81%) of the title compound. ES/MS m/z ($^{35}$Cl) 454 [M+1]$^+$.

Example 5a 2-(4-Chloro-phenyl)-5-[3-methoxy-4-(1-methyl-azetidin-3-yloxy)-phenyl]-5H-thiazolo[5,4-c]pyridin-4-one, hydrochloride salt Dissolve 2-(4-chloro-phenyl)-5-[3-methoxy-4-(1-methyl-azetidin-3-yloxy)-phenyl]-5H-thiazolo[5,4-c]pyridin-4-one (106 g, 234 mmol) in $CHCl_3$ (2.1 L) and cool the solution to 15° C. To the above solution, add dropwise HCl (140 mL, 2 M in diethyl ether) over 10 min. Stir the mixture for one hour and dilute with tert-butyl methyl ether (2 L). Collect the precipitate by filtration and wash the solid with tert-butyl methyl ether (3×660 mL). Dry the solid at room temperature for 4 days under vacuum to give 115 g (100%). ES/MS m/z ($^{35}$Cl) 454 [M+1]$^+$.

Example 5b 2-(4-Chloro-phenyl)-5-[3-methoxy-4-(1-methyl-azetidin-3-yloxy)-phenyl]-5H-thiazolo[5,4-c]pyridin-4-one, fumarate salt Dissolve 2-(4-chloro-phenyl)-5-[3-methoxy-4-(1-methyl-azetidin-3-yloxy)-phenyl]-5H-thiazolo[5,4-c]pyridin-4-one (638 mg, 1.41 mmol) in 1,4-dioxane at 100° C. To the above solution, add a solution of fumaric acid (5.64 mL, 1.41 mmol, 0.25 M in water). Stir the resulting solution at 100° C. for 5 min, then at 50° C. for one hour. Concentrate the solution with a stream of nitrogen gas to ¾ volume. Warm the mixture up to 100° C. until all the solids dissolve, then slowly cool to −10° C. Collect the white precipitate by filtration and wash the solids with cold dioxane (10 mL). Dry the solid at room temperature over the weekend to obtain 500 mg (62%) of the title compound as a fine white powder. ES/MS m/z ($^{35}$Cl) 454 [M+1]$^+$.

Alternate Route to Example 5b

Step 1: 2-Chloro-3-oxo-pentanedioic acid diethyl ester

Dissolve 3-oxo-pentanedioic acid diethyl ester (1122 g, 5.327 mol) in $CH_2Cl_2$ (3 L) and cool to −9° C. To the above solution, slowly add a solution of sulfuryl chloride (374 g, 2.69 mol) in $CH_2Cl_2$ (3 L) over 3 h. Upon completion, add a second charge of sulfuryl chloride (374 g, 2.69 mol) in $CH_2Cl_2$ (3 L) over 4 h. Stir the resulting cooled solution for one hour, then warm to room temperature and stir overnight. Cool the solution in an ice bath and slowly add water (8 L). Stir for 15 min, then separate the layers. Extract the aqueous layer with additional $CH_2Cl_2$. Combine the organic phases and wash with saturated $NaHCO_3$ (3 L). Dry and concentrate the organic solution to obtain 1370 g (105%) of the title compound as a colorless oil. Use the material as-is in the next reaction without further purification. ES/MS m/z ($^{35}$Cl) 235 [M−1]$^−$.

Step 2: 2-(4-Chloro-phenyl)-4-ethoxycarbonylmethyl-thiazole-5-carboxylic acid ethyl ester Dissolve 2-chloro-3-oxo-pentanedioic acid diethyl ester (1370 g, 5.50 mol) in EtOH (8.5 L) and add 4-chloro-thiobenzamide (885 g, 5.00 mol). Heat the mixture to 75° C. and stir mechanically for 5.5 h. Cool the mixture to 45° C., then slowly add water (3.5 L) and stir overnight. Collect the yellow precipitate and wash the solids with 50% EtOH/water (4 L). Dry in an oven to obtain 1505 g (81%) of the title compound. $^1$H NMR (CDCl$_3$, 500 MHz): δ 7.90 (d, 2H, J=7.4), 7.41 (d, 2H, J=7.4), 4.34 (q, 2H, J=6.8), 4.24 (s, 2H), 4.19 (q, 2H, J=7.4), 1.36 (t, 3H, J=6.8), 1.27 (t, 3H, J=6.8).

Step 3: 4-Carboxymethyl-2-(4-chloro-phenyl)-thiazole-5-carboxylic acid

Dissolve 2-(4-chloro-phenyl)-4-ethoxycarbonylmethyl-thiazole-5-carboxylic acid ethyl ester (99 g, 280 mmol) in EtOH (500 mL) and add 2 M NaOH (700 mL, 1400 mmol). Heat the mixture to 50° C. for 1.5 h, then cool the solution in an ice bath, and treat with 2.5 M HCl (1 L) and stir for 2 h. Collect the precipitate by filtration, washing with 50% EtOH/water (500 mL), and then washing with water (1 L). Dry in a vacuum oven overnight at 45° C. to give 80.2 g (95%) of the title compound. $^1$H NMR (DMSO-d6, 500 MHz): δ 13.66 (br s, 1H), 12.55 (br s, 1H), 8.01 (d, 2H, J=8.6), 7.60 (d, 2H, J=8.9), 4.11 (s, 2H).

Step 4: 2-(4-Chloro-phenyl)-4-methoxycarbonylmethyl-thiazole-5-carboxylic acid

Mix 4-carboxymethyl-2-(4-chloro-phenyl)-thiazole-5-carboxylic acid (145 g, 482 mmol) in MeOH (900 mL) and treat with sulfuric acid (1.20 mL, 21.68 mmol). Stir the mixture at reflux overnight and then begin distilling the MeOH to concentrate the solution. Collect about 300 mL of MeOH and then reflux for an additional 5 h. Filter the reaction mixture and cool the filtrate in an ice bath for one hour. Collect the yellow precipitate by filtration and rinse with cool MeOH. Dry the solid in a vacuum oven at 45° C. overnight to give 105 g of the title compound. Concentrate the above filtrate to about 200 mL volume and collect 20 g of additional material. $^1$H NMR (DMSO-d6, 500 MHz): δ 13.72 (br s, 1H), 8.00 (d, 2H, J=8.4), 7.59 (d, 2H, J=8.8), 4.21 (s, 2H), 3.64 (s, 3H).

Step 5: 3-(4-{[2-(4-Chloro-phenyl)-4-methoxycarbonylmethyl-thiazole-5-carbonyl]-amino}-2-methoxy-phenoxy)-azetidine-1-carboxylic acid tert-butyl ester Mix 1-propanephosphonic acid cyclic anhydride (50% in EtOAc) (528.7 g, 831.3 mmol) and THF (1110 mL) and chill to 5° C. Add 2-(4-chloro-phenyl)-4-methoxycarbonylmethyl-thiazole-5-carboxylic acid (185.0 g, 593.43 mmol) followed by 3-(4-amino-2-methoxy-phenoxy)-azetidine-1-carboxylic acid tert-butyl ester (192.2 g, 914.4 mmol). Charge N-methylmorpholine (99 mL, 1247 mmol) dropwise over 15 min and remove the ice bath immediately after the addition. Heat the reaction to 65° C. for 16 h and quench with water (555 mL). Dilute with EtOAc (1110 mL) and partition the layers. Wash with saturated sodium bicarbonate (555 mL) and with brine (555 mL). Distill the organic solvent until <5%

THF remains and then back-add with ethyl acetate as needed to a total of 740 mL solvent at the end of the distillation. Add heptane (230 mL) at 75° C. and seed with authentic product at 55° C. Allow to cool to room temperature, filter, and rinse twice with heptane-EtOAc (2×100 mL, 1:1). Dry in a vacuum oven at 40° C. to obtain 313.5 g (90%) of the title compound as an orange-brown solid. ES/MS m/z ($^{35}$Cl) 586 [M−1]$^-$.

Step 6: 3-(4-{[2-(4-Chloro-phenyl)-4-(2-hydroxy-ethyl)-thiazole-5-carbonyl]-amino}-2-methoxy-phenoxy)-azetidine-1-carboxylic acid tert-butyl ester Charge to a flask under an inert atmosphere a 2 M THF solution of lithium borohydride (1140 mL, 2280 mmol) and apply ice bath cooling. Meanwhile in a separate vessel dissolve 3-(4-{[2-(4-chloro-phenyl)-4-methoxycarbonylmethyl-thiazole-5-carbonyl]-amino}-2-methoxy-phenoxy)-azetidine-1-carboxylic acid tert-butyl ester (2058 g, 3500 mmol) in THF (12.35 L). Agitate until complete dissolution is obtained. Transfer this solution to an addition funnel and begin the slow stream addition to the reducing agent. Once the addition is complete, remove the ice bath and stir for 30-90 min. Quench the reaction by adding acetone (407 g, 7008 mmol). Stir at ambient temperature for 30 min and add ethyl acetate (8230 mL) with water (8230 mL). Separate the layers and wash the upper organic layer a second time with water (8230 mL) followed by 5% brine (8230 mL). Distill off the solvent until <5% solvent composition is THF, by adding EtOAc as needed. Reduce the volume of the slurry to 6200 mL and add heptane (2050 mL). Allow the slurry to slowly cool back to room temperature, filter the precipitate, wash with 1:1 heptane/ethyl acetate and dry to constant weight in a vacuum oven at 40° C. to obtain the title compound (88%). ES/MS m/z ($^{35}$Cl) 560 [M+1]$^+$.

Step 7: 3-{4-[2-(4-Chloro-phenyl)-4-oxo-4H-thizolo[5,4-c]pyridine-5-yl]-2-methoxy-phenoxy}-azetidine-1-carboxylic acid tent-butyl ester Charge to the reaction vessel 3-(4-{[2-(4-chloro-phenyl)-4-(2-hydroxy-ethyl)-thiazole-5-carbonyl]-amino}-2-methoxy-phenoxy)-azetidine-1-carboxylic acid tert-butyl ester (2520 g, 4499 mmol), DMSO (5040 mL), and triethylamine (1932 g, 18901 mmol). Cool the brown slurry to 15° C. In a separate vessel, dissolve sulfur trioxide-pyridine complex (2923 g, 17997 mmol) in DMSO (12.6 L). Add slowly the SO$_3$-pyridine solution to the reaction mixture in such a manner as to keep any exotherm below 22° C. When the addition is complete heat the reaction to 65° C. for 16 h. After completion of the reaction maintain the temperature at 65° C. and add water (17.64 L) in a slow to moderate stream. Stir the resulting slurry at 65° C. for 90 min and filter off the crude product without cooling. Rinse the crude cake twice with water, then give the wet cake a displacement wash with ice cold methanol. Pull dry the MeOH wet cake for 30 min and then return it to the reaction vessel and slurry in methanol (20.16 L). Heat to 65° C. for 10 min, slowly cool back to room temperature, filter, wash with methanol, and dry to constant weight in a vacuum oven at 40° C. to obtain 2192 g (90%) of the title compound. ES/MS m/z ($^{35}$Cl) 484 [M-tert+1]$^+$.

Step 8: 5-[4-(Azetidin-3-yloxy)-3-methoxy-phenyl]-2-(4-chloro-phenyl)-5H-thiazolo[5,4-c]pyridin-4-one, hydrochloride salt To a reaction vessel charge 3-{[2-(4-chloro-phenyl)-4-oxo-4H-thizolo[5,4-c]pyridine-5-yl]-2-methoxy-phenoxy}-azetidine-1-carboxylic acid tert-butyl ester (5.00 g, 9.26 mmol) and n-propanal (100 mL) and stir as a thin slurry. Add 37% HCl (2.0 mL, 23.2 mmol) at room temperature in one portion and heat to 65° C. for 16 h. Remove from heat and cool to room temperature. Filter and rinse with n-PrOH (10 mL) to obtain an off-white solid. Dry the filter cake in a vacuum oven at 45° C. to constant weight to obtain 4.216 g (96%) of the title compound. ES/MS m/z ($^{35}$Cl) 440 [M+1]$^+$.

Step 9: 2-(4-Chloro-phenyl)-5-[3-methoxy-4-(1-methyl-azetidin-3-yloxy)-phenyl]-5H-thiazolo[5,4-c]pyridin-4-one Combine methanol (480 mL), 3-{4-[2-(4-chloro-phenyl)-4-oxo-4H-thizolo[5,4-c]pyridine-5-yl]-2-methoxy-phenoxy}-azetidine-1-carboxylic acid tert-butyl ester (60.00 g, 111.1 mmol), and chloroform (480 mL). To this solution add slowly 35% aqueous HCl (28.4 g, 277 mmol). Heat the reaction mixture to 50° C. for 15 h. Cool the reaction mixture to 10° C. A thick slurry arises around 35° C. Once at 10° C., add formaldehyde (27.33 g, 333 mmol) and the thick slurry becomes thinner while stirring for 2.5 h. Add sodium triacetoxyborohydride (76.53 g, 361 mmol) in three equal portions and warm the reaction mixture to room temperature. Charge sodium carbonate solution to the reaction until pH=8.1 and allow the layers to separate. Wash the organic layer with water (300 mL). Distill off the solvent until the solution volume is 240 mL and add back ethyl acetate (240 mL) to obtain a nice slurry. Cool reaction to room temperature and filter. Rinse with ethyl acetate (180 mL), and dry to constant weight under vacuum at 50° C. to obtain 45.57 g (91%) of the title compound. ES/MS m/z ($^{35}$Cl) 454 [M+1]$^+$.

Step 10: 2-(4-Chloro-phenyl)-5-[3-methoxy-4-(1-methyl-azetidin-3-yloxy)-phenyl]-5H-thiazolo[5,4-c]pyridin-4-one, fumarate salt Dissolve fumaric acid (59.41 g, 0.5118 mol) methanol/water (1900 mL, 1/1) by heating to 60° C. In a separate vessel dissolve 2-(4-chloro-phenyl)-5-[3-methoxy-4-(1-methyl-azetidin-3-yloxy)-phenyl]-5H-thiazolo[5,4-c]pyridin-4-one (200.0 g, 0.4406 mol) in methanol (2000 mL) and heat to 65° C. Add fumaric acid solution hot as quickly as possible. Allow the temperature to recover to 65° C. and hold for 15 min. Cool to 25° C. at 0.25° C./min and hold for one hour. Filter and wash the reactor twice with methanol (100 mL), and rinse the filter cake twice with methanol (250 mL) each. Dry under vacuum at 40° C. until constant weight to provide 223 g (89%) of the title compound.

Preparation 33

3,4-Difluoro-thiobenzamide

Dissolve 3,4-difluorobenzamide (4.95 g, 31.5 mmol) in diethyl ether (70 mL) and cool the mixture to 0° C. Add phosphorus pentasulfide (7.0 g, 31.5 mmol) and warm the mixture to room temperature overnight. Filter the mixture and concentrate the filtrate to obtain 5.5 g (100%) of a yellow solid. $^1$H NMR (300 MHz, DMSO-d6) δ: 9.99 (bs, 1H), 9.54 (bs, 1H), 7.89 (m, 1H), 7.75 (m, 1H), 7.46 (m, 1H).

Prepare the thiazolo-pyridone compounds in the table below, using 4-trifluoromethyl-thiobenzamide and 3,4-difluoro-thiobenzamide, by essentially following the procedures in the alternate route of Example 5b, Steps 1 to 7.

| Prep | Product (Chemical name) | ES/MS/m/z |
|---|---|---|
| 34 | 3-{2-Methoxy-4-[4-oxo-2-(4-trifluoromethyl-phenyl)-4H-thiazolo[5,4-c]pyridin-5-yl]-phenoxy}-azetidine-1-carboxylic acid tert-butyl ester | 518.0 [M-tBu + 1]+ |
| 35 | 3-{4-[2-(3,4-Difluoro-phenyl)-4-oxo-4H-thiazolo[5,4-c]pyridin-5-yl]-2-methoxy-phenoxy}-azetidine-1-carboxylic acid tert-butyl ester | 486.0 [M-tBu + 1]+ |

Preparation 36

5-[4-(Azetidin-3-yloxy)-3-methoxy-phenyl]-2-(4-trifluoromethyl-phenyl)-5H-thiazolo[5,4-c]pyridin-4-one Dissolve 3-{2-methoxy-4-[4-oxo-2-(4-trifluoromethyl-phenyl)-4H-thiazolo[5,4-c]pyridin-5-yl]-phenoxy}-azetidine-1-carboxylic acid tert-butyl ester (1.3 g, 2.27 mmol) in dichloromethane (12 mL) and slowly add trifluoroacetic acid (6 mL). Stir the mixture for one hour and then evaporate. Apply the residue to a 10 g SCX column with dichloromethane. Wash the column with methanol then elute the material using 1:1 dichloromethane:2N ammonia/methanol. Concentrate to give 0.909 g (85%) of the desired product as a white solid. MS/ES m/z 474.0 [M+1]+.

Prepare the free amine compound in the table below by essentially following the procedure in Preparation 36.

| Prep | Product (Chemical name) | ES/MS/m/z |
|---|---|---|
| 37 | 5-[4-(Azetidin-3-yloxy)-3-methoxy-phenyl]-2-(3,4-difluoro-phenyl)-5H-thiazolo[5,4-c]pyridin-4-one | 442.0 [M + 1]+ |

Example 6

5-[4-(1-Cyclobutyl-azetidin-3-yloxy)-3-methoxy-phenyl]-2-(4-trifluoromethyl-phenyl)-5H-thiazolo[5,4-c]pyridin-4-one Dissolve 5-[4-(azetidin-3-yloxy)-3-methoxy-phenyl]-2-(4-trifluoromethyl-phenyl)-5H-thiazolo[5,4-c]pyridin-4-one (0.909 g, 1.92 mmol) in dichloroethane (25 mL) and add cyclobutanone (0.502 mL, 6.72 mmol), sodium triacetoxyborohydride (0.814 g, 3.84 mmol), and acetic acid (0.22 mL, 3.84 mmol). Stir the mixture overnight, add saturated sodium bicarbonate, and extract with dichloromethane (3×). Dry the mixture using sodium sulfate, filter, and concentrate. Purify via silica gel chromatography using a 0-4.5% gradient of 2N ammonia in methanol/dichloromethane to give 0.400 g (39%) of the desired product. MS/ES m/z 528.0 [M+1]+.

Prepare the compounds in the table below by essentially following the procedure in Example 7 using the appropriate ketone.

| Ex | Product (Chemical name) | ES/MS/m/z or NMR |
|---|---|---|
| 7 | 5-[4-(1-Cyclobutyl-azetidin-3-yloxy)-3-methoxy-phenyl]-2-(3,4-difluoro-phenyl)-5H-thiazolo[5,4-c]pyridin-4-one | 496.0 [M + 1]+ |
| 8 | 2-(4-Chloro-phenyl)-5-[4-(1-isopropyl-azetidin-3-yloxy)-3-methoxy-phenyl]-5H-thiazolo[5,4-c]pyridin-4-one | 1H NMR (CDCl3, 500 MHz) δ: 8.02 (d, 2H, J = 8.3), 7.48 (d, 2H, J = 8.8), 7.40 (d, 1H, J = 7.4), 6.97 (d, 1H, J = 2.2), 6.90 (dd, 1H, J = 2.6, 8.8), 6.74 (d, 1H, J = 8.8), 4.81 (m, 1H), 3.89 (m, 2H), 3.88 (s, 3H), 3.15 (m, 2H), 2.43 (m, 1H), 0.98 (d, 6H, J = 6.1). |

Example 9

2-(4-Chloro-phenyl)-5-{3-methoxy-4-[1-(tetrahydro-pyran-4-yl)-azetidin-3-yloxy]-phenyl}-5H-thiazolo[5,4-c]pyridin-4-one, hydrochloride salt Suspend 5-[4-(azetidin-3-yloxy)-3-methoxy-phenyl]-2-(4-chloro-phenyl)-5H-thiazolo[5,4-c]pyridin-4-one (50 mg, 0.11 mmol) in MeOH (5.68 mL). Add tetrahydro-4H-pyran-4-one (15.7 μL, 0.17 mmol) and acetic acid (9.8 μL, 0.17 mmol) and stir at room temperature for 10 min. Add sodium cyanoborohydride (7.1 mg, 0.11 mmol) and stir at room temperature for 6 h. Add dichloromethane to the reaction mixture to dissolve the solid material. Pour onto a 2 g SCX2 ion exchange column wet with MeOH and elute under gravity. Elute SCX cartridge with MeOH (approximately 3 volumes) under reduced pressure and discard. Elute SCX cartridge with 7N NH3 in MeOH:dichloromethane (1:1) (approximately 5 volumes) under reduced pressure and then concentrate in vacuo. Dissolve the resultant solid in dichloromethane (5 mL) and add 4 N HCl in dioxane solution (25 μL). Evaporate the solvent and suspend the solid in water. Freeze-dry to give (51 mg, 83%) of the title compound as a white solid. ES/MS m/z (35Cl) 524 [M+1]+.

Prepare the compounds in the table below, Examples 10 to 17, by essentially following the procedure in Example 9 using the appropriate aldehyde or ketone.

| Ex | Product (Chemical name) | ES/MS/m/z |
|---|---|---|
| 10 | 2-(4-Chloro-phenyl)-5-[4-(1-cyclohexyl-azetidin-3-yloxy)-3-methoxy-phenyl]-5H-thiazolo[5,4-c]pyridin-4-one, hydrochloride salt | (35Cl) 522 [M + 1]+ |
| 11 | 2-(4-Chloro-phenyl)-5-[4-(1-cyclopentyl-azetidin-3-yloxy)-3-methoxy-phenyl]-5H-thiazolo[5,4-c]pyridin-4-one, hydrochloride salt | (35Cl) 508 [M + 1]+ |
| 12 | 5-[4-(1-Benzyl-azetidin-3-yloxy)-3-methoxy-phenyl]-2-(4-chloro-phenyl)-5H-thiazolo[5,4-c]pyridin-4-one, hydrochloride salt | (35Cl) 530 [M + 1]+ |
| 13 | 2-(4-Chloro-phenyl)-5-[3-methoxy-4-(1-thiazol-2-ylmethyl-azetidin-3-yloxy)-phenyl]-5H-thiazolo[5,4-c]pyridin-4-one, hydrochloride salt | (35Cl) 537 [M + 1]+ |

-continued

| Ex | Product (Chemical name) | ES/MS/m/z |
|---|---|---|
| 14 | 2-(4-Chloro-phenyl)-5-{3-methoxy-4-[1-(tetrahydro-thiopyran-4-yl)-azetidin-3-yloxy]-phenyl}-5H-thiazolo[5,4-c]pyridin-4-one, hydrochloride salt | ($^{35}$Cl) 540 [M + 1]$^+$ |
| 15 | 2-(4-Chloro-phenyl)-5-[4-(1-cyclopropylmethyl-azetidin-3-yloxy)-3-methoxy-phenyl]-5H-thiazolo[5,4-c]pyridin-4-one, hydrochloride salt | ($^{35}$Cl) 494 [M + 1]$^+$ |
| 16 | 2-(4-Chloro-phenyl)-5-{4-[1-(4,4-difluoro-cyclohexyl)-azetidin-3-yloxy]-3-methoxy-phenyl}-5H-thiazolo[5,4-c]pyridin-4-one, hydrochloride salt | ($^{35}$Cl) 558 [M + 1]$^+$ |
| 17 | 2-(4-Chlorophenyl)-5-{3-methoxy-4-[1-(2-hydroxycyclohexyl)azetidin-3-yloxy]-phenyl}-5H-thiazolo[5,4-c]pyridin-4-one, hydrochloride salt | ($^{35}$Cl) 538 [M + 1]$^+$ |

Example 18a & 18b 2-(4-Chloro-phenyl)-5-[3-methoxy-4-(1-methyl-1-oxy-azetidin-3-yloxy)-phenyl]-5H-thiazolo[5,4-c]pyridin-4-one, Isomer 1 & Isomer 2

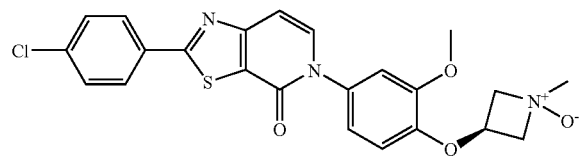

Dissolve 2-(4-chloro-phenyl)-5-[3-methoxy-4-(1-methyl-azetidin-3-yloxy)-phenyl]-5H-thiazolo[5,4-c]pyridin-4-one (402 mg, 0.886 mmol) in CH$_2$Cl$_2$ (9 mL) and cool to 0° C. Treat the solution with m-chloroperoxybenzoic acid (190 mg, 1.10 mmoles). Stir the solution at 0° C. for 30 min and then collect the precipitate by filtration and wash with additional CH$_2$Cl$_2$ (approximately 10 mL) and dry in vacuo. Purify the mixture of N-oxides (cis & trans) by flash chromatography, eluting with 25% MeOH (2N NH$_3$)/CH$_2$Cl$_2$ to give pure stereoisomer 1 (220 mg). Concentrate the filtrate from above and purify by flash chromatography, eluting with 25% MeOH (2N NH$_3$)/CH$_2$Cl$_2$ to give pure stereoisomer 1 (110 mg) and pure stereoisomer 2 (47 mg). Combine and triturate isomer 1 materials with ether, then dry under vacuum to give 320 mg. Triturate isomer 2 with ether, then dry under vacuum to give 16 mg.
Isomer 1; ES/MS m/z ($^{35}$Cl) 470 [M+1]$^+$; Example 18a.
Isomer 2; ES/MS m/z ($^{35}$Cl) 470 [M+1]$^+$; Example 18b.

Example 19

2-(4-Chloro-phenyl)-5-{4-[1-(2,2-difluoro-ethyl)-azetidin-3-yloxy]-3-methoxy-phenyl}-5H-thiazolo[5,4-c]pyridin-4-one, hydrochloride salt Dissolve N-methy-N-methoxydifluoroacetamide (1.0 mL, 6.97 mmol) in dry THF (6.17 mL). Chill the solution to 0° C. and add diisobutylaluminium hydride (1.39 mL, 1.39 mmol). Stir for one hour or until complete by TLC (1:1 EtOAc/hexane, KMnO$_4$ stain used to detect non-uv aldehyde formation). Add 5% HCl/EtOH solution to the reaction mixture and extract with 1:1 CH$_2$Cl$_2$/Et$_2$O. Combine the organic layers and wash with brine. Dry and filter with Na$_2$SO$_4$. Concentrate to minimal amounts of organic solvent. (Note: do not dry aldehyde due to low molecular weight and possible high volatility).

Add the aldehyde solution to a suspension of 5-[4-(azetidin-3-yloxy)-3-methoxy-phenyl]-2-(4-chloro-phenyl)-5H-thiazolo[5,4-c]pyridin-4-one (350 mg, 0.800 mmol) in MeOH (2.65 mL). Add acetic acid (0.227 mL, 3.98 mmol) and stir vigorously. Add sodium cyanoborohydride (131.5 mg, 2.0 mmol). Stir overnight at room temperature. Add saturated NaHCO$_3$ solution (10 mL), stir for 30 min, and then extract with CH$_2$Cl$_2$ (2×10 mL). Dry, filter, and concentrate the organic solution. Purify the crude material by flash chromatography, using 0-10% MeOH (2M NH$_3$)/CH$_2$Cl$_2$ as eluent, to give a white solid. Redissolve in CHCl$_3$ and add HCl/Et$_2$O (0.320 mL). Filter the HCl salt to give 177 mg (41%) of the title compound. ES/MS m/z ($^{35}$Cl) 504.0 [M+1]$^+$.

Example 20

2-(4-Chloro-phenyl)-5-{3-methoxy-4-[1-(3,3,3-trifluoro-propyl)-azetidin-3-yloxy]-phenyl}-5H-thiazolo[5,4-c]pyridin-4-one, hydrochloride salt Add 3,3,3-trifluoropropanal (120 mg, 1.06 mmol) to a suspension of 5-[4-(azetidin-3-yloxy)-3-methoxy-phenyl]-2-(4-chloro-phenyl)-5H-thiazolo[5,4-c]pyridin-4-one (390 mg, 0.89 mmol) in MeOH (2.96 mL). Add acetic acid (0.254 mL, 4.43 mmol) and stir vigorously. Add sodium cyanoborohydride (146.6 mg, 2.22 mmol). Stir overnight at room temperature. Add saturated NaHCO$_3$ (10 mL) and stir for 30 min. Extract the mixture with CH$_2$Cl$_2$ (2×10 mL). Combine the organic layer and wash with water (5 mL). Dry, filter, and concentrate the organic solution. Purify the crude material by flash chromatography, using 0-40% THF (1% NH$_3$/MeOH) in heptane as eluent, to give a white solid. Redissolve in CHCl$_3$ and add HCl/Et$_2$O (0.32 mL). Filter the HCl salt to provide 37 mg (7%) of the title compound. ES/MS m/z 536.0 ($^{35}$Cl) [M+1]$^+$.

Prepare the compound in the table below by essentially following the procedure as described in Example 20.

| Ex | Product (Chemical Name) | ES/MS m/z |
|---|---|---|
| 21 | 2-(4-Chloro-phenyl)-5-[3-fluoro-4-(1-methyl-azetidin-3-yloxy)-phenyl]-5H-thiazolo[5,4-c]pyridin-4-one, hydrochloride salt | ($^{35}$Cl) 442 [M + 1]$^+$ |

Preparation 38

3-(2-Bromo-thiazol-4-yl)-acrylic acid methyl ester

Dissolve 2-bromothiazole-4-carbaldehyde (3.00 g, 15.62 mmol) in tetrahydrofuran (52 mL) and add methyl(triphenylphosphoranylidene)acetate (5.33 g, 15.62 mmol). Stir the mixture overnight at room temperature. Dilute the mixture with water and extract twice using diethyl ether. Dry the combined organics over sodium sulfate, filter, and concentrate. Purify via silica gel chromatography using a 0-30% gradient of EtOAc/hexanes to give 3.13 g (81%) of the title compound as a white solid.

Preparation 39

3-(2-Bromo-thiazol-4-yl)-acrylic acid

Dissolve 3-(2-bromo-thiazol-4-yl)-acrylic acid methyl ester (5.9 g, 23.78 mmol) in tetrahydrofuran (48 mL) and add a solution of lithium hydroxide (636 mg, 26.16 mmol) in water (10 mL). Stir the mixture overnight. Extract the mixture with ethyl acetate and wash twice with water. Acidify the aqueous layer with 1N HCl in water until the mixture is at pH 3-4. Filter the resulting white solid, then wash the solid with ethyl acetate, followed by diethyl ether and then water. Dry the white solid to give 5.05 g (91%) of the desired material.

Preparation 40

2-Bromo-5H-thiazolo[5,4-c]pyridin-4-one

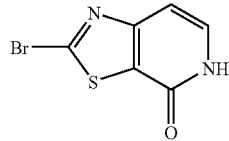

Suspend 3-(2-bromo-thiazol-4-yl)-acrylic acid (2.00 g, 8.54 mmol) in dichloromethane (17 mL) and add oxalyl chloride (1.48 mL, 17.09 mmol) and 2 drops of dimethylformamide. Stir the mixture at room temperature for 2 h and evaporate. Dissolve sodium azide (1.67 g, 25.63 mmol) in water (12 mL) and acetone (12 mL) and cool to 0° C. Dissolve the acid chloride in 1,4-dioxane (12 mL) and add to the sodium azide. Stir the mixture for one hour at 0° C. Dilute the mixture with water and extract three times with ethyl acetate. Dry the combined organic layers with sodium sulfate, filter and evaporate to give a yellow solid.

Heat Dowtherm® A (20 mL) to 230° C. and add the yellow solid from above in dioxane (12 mL). When the addition is complete, stir the mixture at 230° C. for one hour. Cool the mixture to room temperature and stir overnight. Dilute the mixture with diethyl ether, filter the resulting brown solid, and wash with diethyl ether three times. Dissolve the bulk of the solid with tetrahydrofuran and filter off the remaining brown materials. Concentrate and purify via silica gel chromatography using a 0-10% gradient of methanol/dichloromethane to give 0.425 g (22% yield) of the title compound as a yellow solid. $^1$H NMR (300 MHz, DMSO-d6) δ 11.95 (bs, 1H), 7.44 (d, 1H, J=7.1 Hz), 6.82 (d, 1H, J=7.1 Hz).

Preparation 41

2-(4-Cyclopropoxy-phenyl)-5H-thiazolo[5,4-c]pyridin-4-one

Dissolve 2-bromo-5H-thiazolo[5,4-c]pyridin-4-one (0.218 g, 0.934 mmol) in dimethoxyethane (5 mL) followed by addition of EtOH (1 mL) and water (1 mL). Add 4-cylcopropoxyphenylboronic acid (prepare as described in Olofsson, K. et al, WO 2005123673) (0.185 g, 1.04 mmol) followed by 2M $Na_2CO_3$ (1 mL, 2 mmol). Allow dry argon gas to bubble through the reaction mixture for 15-20 min. Add $Pd(PPh_3)_4$ (33 mg, 0.27 μmol) and then warm to 85° C. under an argon atmosphere. After 18 h, evaporate the mixture to a slurry. Dilute the mixture with water and stir for one hour. Filter and wash the solids with diethyl ether, then water, and then diethyl ether again. Dry the solids at room temperature overnight to give the desired material as a brown solid (0.214 g, 80%). $^1$H NMR (300 MHz, DMSO-d6) δ 11.7 (bs, 1H), 8.01 (d, 2H, J=8.8 Hz), 7.42 (d, 1H, J=6.9 Hz), 7.18 (d, 2H, J=8.8 Hz), 6.81 (d, 1H, J=6.9 Hz), 3.93 (m, 1H), 0.80 (m, 2H), 0.67 (m, 2H).

Prepare the thiazole pyridone in the table below by essentially following the procedure as described in Preparation 41.

| Prep | Product (Chemical Name) | ES/MS m/z |
|------|-------------------------|-----------|
| 42 | 4-(4-Oxo-4,5-dihydro-thiazolo[5,4-c]pyridin-2-yl)-benzonitrile | 254.0 [M + 1]$^+$ |

Preparation 43

2-(4-Chloro-phenyl)-4-(2-hydroxy-ethyl)-thiazole-5-carboxylic acid 2,4-dimethoxy-benzylamide Dissolve 2,4-dimethoxybenzylamine (22.4 g, 134.0 mmol) in $CH_2Cl_2$ (300 mL) and cool to 0° C. To the above solution, slowly add a solution of trimethylaluminum (110 mL, 220 mmol; 2 M in toluene) over 35 min while keeping the temperature below 10° C. Stir the resulting solution at room temperature for 45 min and then re-cool to 0° C. Add 2-(4-chloro-phenyl)-6,7-dihydro-pyrano[4,3-d]thiazol-4-one (52.2 g, 120.6 mmol), then allow the resulting slurry to warm to room temperature and stir overnight. Cool the reaction and carefully quench with saturated Rochelle's salt solution (300 mL) over 30 min. Add $CH_2Cl_2$ (750 mL), water (400 mL) and diatomaceous earth (100 g) and stir the mixture at room temperature for 30 min, then filter. Collect the solids and triturate with $CH_2Cl_2$ (1 L) at 35° C. for 3 h, then filter. Concentrate the filtrate to obtain the title compound (32.2 g). Repeat the trituration step with the second solid cake and obtain an additional 20 g of title compound (90% total yield). $^1$H NMR (400 MHz, DMSO-d6) δ 9.01 (br s, 1H), 7.96 (d, 2H, J=8.5), 7.57 (d, 2H, J=8.5), 7.15 (d, 1H, J=7.9), 6.57 (d, 1H, J=2.6), 6.48 (dd, 1H, J=2.6, 8.5), 5.34 (t, 1H, J=4.3), 4.34 (d, 2H, J=6.6), 3.81 (s, 3H), 3.79 (m, 2H), 3.75 (s, 3H), 3.11 (t, 3H, J=6.6).

Preparation 44

2-(4-Chloro-phenyl)-5-(2,4-dimethoxy-benzyl)-5H-thiazolo[5,4-c]pyridin-4-one Mix 2-(4-chloro-phenyl)-4-(2-hydroxy-ethyl)-thiazole-5-carboxylic acid 2,4-dimethoxy-benzylamide (19.7 g, 45.5 mmol) with EtOAc (400 mL) and treat the resulting slurry with 1-hydroxy-1-oxo-1H-benzo[d][1,2]iodoxol-3-one (36.0 g, 57.8 mmol). Stir the mixture at 60° C. for 1.5 h. Add additional 1-hydroxy-1-oxo-1H-benzo[d][1,2]iodoxol-3-one (18.0 g, 28.9 mmol) and stir at 70° C. overnight. Cool the mixture to room temperature and then dilute with $CH_2Cl_2$ (600 mL). Filter the mixture and wash the solids with additional $CH_2Cl_2$ (3×500 mL). Wash the filtrate with $NaHCO_3$ (4×300 mL) and water (300 mL). Dry the organic portion, filter, and concentrate in vacuo. Purify the crude material by flash chromatography, using 0.5% MeOH/$CH_2Cl_2$ as eluent, to give 13.1 g (70%) of the title compound as a light yellow-orange solid. $^1$H NMR (400 MHz, CDCl$_3$) δ7.99 (d, 2H, J=8.1), 7.50 (d, 1H, J=7.4), 7.45 (d, 2H, J=8.8), 7.38 (d, 1H, J=8.8), 6.84 (d, 1H, J=6.4), 6.46 (m, 2H), 5.16 (s, 2H), 3.84 (s, 3H), 3.78 (s, 3H).

Preparation 45

2-(4-Chloro-phenyl)-5H-thiazolo[5,4-c]pyridin-4-one

Mix 2-(4-chloro-phenyl)-5-(2,4-dimethoxy-benzyl)-5H-thiazolo[5,4-c]pyridin-4-one (24.6 g, 59.6 mmol) in trifluoroacetic acid (143 mL) and heat at 70° C. for 2 h. Cool the mixture to room temperature and add water (325 mL) and saturated NaHCO$_3$ (710 mL) with stirring. Add acetone (180 mL) and stir the resulting slurry for one hour at room temperature. Filter and wash the solids with water (110 mL) and then acetone (110 mL). Dry the solids in a vacuum oven at 60° C. overnight. Triturate the solids three times with CH$_3$CN (700 mL) at 60° C. and filter. Dry the solids in a vacuum oven at 60° C. overnight to obtain 18.3 g (117%) of the title compound that still contains salt impurities. $^1$H NMR (400 MHz, DMSO-d6) δ11.86 (s, 1H), 8.12 (d, 2H, J=8.2), 7.65 (d, 2H, J=8.7), 7.49 (t, 1H, J=6.0), 6.91 (1H, J=6.6).

Preparation 46

3-(4-Bromo-2-methoxy-phenoxy)-azetidine-1-carboxylic acid tent-butyl ester

Add sodium hydride (2.77 g, 60% w/w, 69.2 mmol) to a solution of 3-hydroxy-azetidine-1-carboxylic acid tert-butyl ester (10.9 g, 62.9 mmol) in dimethyl sulfoxide (100 mL). Stir the mixture for 30 min and then add 3-bromo-6-fluoroanisole (15.5 g, 75.5 mmol). Heat the mixture to 65° C. overnight. Cool the mixture to room temperature and then dilute the solution with saturated ammonium chloride and brine and extract with ethyl acetate. Wash the organics five times with brine, then dry over sodium sulfate and filter. Concentrate and purify via silica gel chromatography using a 0-45% gradient of ethyl acetate/hexane to give 10.4 g (46%) of the title compound as a clear oil.

Preparation 47

3-(4-Bromo-2-methoxy-phenoxy)-azetidine

Dissolve 3-(4-bromo-2-methoxy-phenoxy)-azetidine-1-carboxylic acid tert-butyl ester (2.9 g, 8.10 mmol) in dichloromethane (45 mL) and slowly add trifluoroacetic acid (15 mL). Stir the mixture for one hour and then evaporate. Apply the residue to two 10 g SCX columns with methanol. Wash the columns with methanol, then elute the material using 2N ammonia/methanol. Concentrate to give 2.09 g (88%) of the title compound as a clear oil.

Preparation 48

3-(4-Bromo-2-methoxy-phenoxy)-1-cyclobutyl-azetidine

Dissolve 3-(4-bromo-2-methoxy-phenoxy)-azetidine (1.84 g, 7.13 mmol) in dichloroethane (80 mL). Add cyclobutanone (1.86 mL, 25 mmol), sodium triacetoxyborohydride (3.02 g, 14.3 mmol) and acetic acid (0.82 mL, 14.3 mmol). Stir the mixture overnight, then add saturated sodium bicarbonate and extract three times using dichloromethane. Dry the combined organic portions over sodium sulfate, filter, and concentrate. Purify by silica gel chromatography using a 0-3% gradient of methanol/dichloromethane to give 1.26 g (56%) of the title compound.

Preparation 49

3-(4-Bromo-phenoxy)-azetidine-1-carboxylic acid tent-butyl ester

Combine 1-bromo-4-fluorobenzene (10.1 g, 57.7 mmol) and tert-butyl 3-hydroxyazetidine-1-carboxylate (5.0 g, 28.9 mmol) in THF (144 mL) and stir at room temperature. Add slowly potassium tert-butoxide (75.7 mL, 57.7 mmol, 1M in THF). Heat the mixture at 70° C. for 4 h. Monitor the reaction completion via gas chromatography. Cool the mixture to room temperature and quench with water. Dilute the mixture with ether. Wash the organic portion with saturated NH$_4$Cl. Back extract the aqueous with ether. Dry the combined organics with Na$_2$SO$_4$, filter, and concentrate. Purify the material by flash chromatography using 5-10% EtOAc/hexanes to give 1.84 g (19% yield) of the title compound as a white solid.

Example 22

5-[4-(1-Cyclobutyl-azetidin-3-yloxy)-3-methoxy-phenyl]-2-(4-cyclopropoxy-phenyl)-5H-thiazolo[5,4-c]pyridin-4-one Suspend 3-(4-bromo-2-methoxy-phenoxy)-1-cyclobutyl-azetidine (0.233 g, 0.746 mmol), 2-(4-cyclopropoxy-phenyl)-5H-thiazolo[5,4-c]pyridin-4-one (0.212 g, 0.746 mmol), cesium carbonate (0.486 g, 1.49 mmol), and 1,4-dioxane (5 mL) in a flask. Sparge with subsurface nitrogen for 15 min. Charge this mixture with copper (I) iodide (0.057 g, 0.298 mmol) followed by sym-dimethylethylene diamine (64 µL, 0.596 mmol). Heat the mixture to 110° C. under nitrogen overnight.

Bring the reaction to room temperature and dilute with water followed by ammonium hydroxide. Extract the mixture using dichloromethane (3×). Dry the combined organics using sodium sulfate, filter, and concentrate. Purify the material by flash chromatography using 4.5% MeOH (2N NH$_3$)/CH$_2$Cl$_2$ to give 83 mg (22%) of the title compound as a white solid. MS/ES m/z 516.0 [M+1]$^+$.

Prepare the thiazole pyridone in the table below by essentially following the procedure as described in Example 22.

| Ex or Prep | Product (Chemical Name) | ES/MS m/z |
|---|---|---|
| 23 | 4-{5-[4-(1-Cyclobutyl-azetidin-3-yloxy)-3-methoxy-phenyl]-4-oxo-4,5-dihydro-thiazolo[5,4-c]pyridin-2-yl}-benzonitrile | 485.0 [M + 1]$^+$ |
| Prep 50 | 3-{4-[2-(4-Chloro-phenyl)-4-oxo-4H-thiazolo[5,4-c]pyridin-5-yl]-phenoxy}-azetidine-1-carboxylic acid tert-butyl ester | 454.0 [M-tertBu + 1]$^+$ |

Example 24

2-(4-chlorophenyl)-5-(4-(1-methylazetidin-3-yloxy) phenyl)thiazolo[5,4-c]pyridin-4(5H)-one, succinate salt

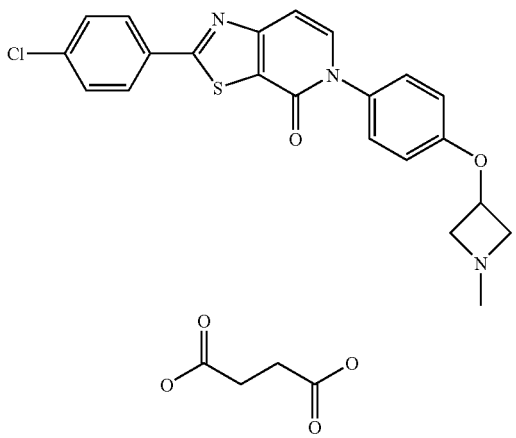

Add 37% aqeuous HCl (0.25 mL, 2.94 mmol) to a solution of tert-butyl 34442-(4-chlorophenyl)-4-oxothiazolo[5,4-c] pyridin-5(4H)-yl)phenoxy)azetidine-1-carboxylate (0.5 g, 0.98 mmol) in methanol (20 mL). Heat the mixture at 50° C. for 2 h. Cool the mixture to 10° C. and then add 37% formaldehyde (0.37 mL, 4.98 mmol) followed by sodium triacetoxyborohydride (1.3 g, 5.88 mmol). Stir the mixture at room temperature for 2 h. Dilute the mixture with dichloromethane. Wash with saturated Na$_2$CO$_3$ solution and water. Dry the organic portion over Na$_2$SO$_4$, filter, and concentrate. Purify the crude material by flash chromatography, using 5-10% MeOH/CH$_2$Cl$_2$ as eluent.

Dissolve the solid product in dichloromethane. Add butanedioic acid (1 eq). Stir the solution for 15 min and then concentrate to dryness. Filter the solid with ether to give 0.14 g (26%) of the title compound. ES/MS m/z ($^{35}$Cl) 424 [M+1]$^+$.

Preparation 51

5-(4-(azetidin-3-yloxy)phenyl)-2-(4-chlorophenyl) thiazolo[5,4-c]pyridin-4(5H)-one Add 37% aqueous HCl (0.25 mL, 2.94 mmol) to a solution of tert-butyl 34442-(4-chlorophenyl)-4-oxothiazolo[5,4-c] pyridin-5 (4H)-yl)phenoxy)azetidine-1-carboxylate (0.5 g, 0.98 mmol) in methanol (20 mL) and chloroform (20 mL). Heat the mixture at 50° C. for 2 h. Cool the mixture to room temperature and dilute with dichloromethane. Wash the mixture with saturated Na$_2$CO$_3$ solution and water. Dry the organic portion over Na$_2$SO$_4$, filter, and concentrate to give 0.44 g (97%) of the title compound. ES/MS m/z ($^{35}$Cl) 410 [M+1]$^+$.

Example 25

2-(4-chlorophenyl)-5-(4-(1-cyclobutylazetidin-3-yloxy)phenyl)thiazolo[5,4-c]pyridin-4(5H)-one, hydrochloride salt Add cyclobutanone (0.4 mL, 5.4 mmol) to a solution of 5-(4-(azetidin-3-yloxy)phenyl)-2-(4-chlorophenyl)thiazolo [5,4-c]pyridin-4(5H)-one (0.44 g, 1.08 mmol) in methanol (54 mL) and acetic acid (0.31 mL, 5.4 mmol). Stir the mixture at room temperature for one hour, add sodium triacetoxyborohydride (1.4 g, 6.48 mmol) and continue stirring at room temperature overnight. Dilute the mixture with dichloromethane, then wash with saturated NaHCO$_3$ solution and water. Dry the organic portion over Na$_2$SO$_4$, filter, and concentrate. Purify the crude material by flash chromatography, using 0-10% MeOH/CH$_2$Cl$_2$ as eluent. Dissolve the solid with dichloromethane and add 1 M HCl/ether (1 eq). Stir the solution for 15 min. Concentrate the solid and filter with ether to give 0.31 g (58%) of the title compound. ES/MS m/z ($^{35}$Cl) 464 [M+1]$^+$.

Example 26

5-[4-(Azetidin-3-yloxy)-3-methoxy-phenyl]-2-(4-chloro-phenyl)-6,7-dihydro-5H-thiazolo[5,4-c]pyridin-4-one Dissolve 3-{4-[2-(4-chloro-phenyl)-4-oxo-6,7-dihydro-4H-thiazolo[5,4-c]pyridin-5-yl]-2-methoxy-phenoxy}-azetidine-1-carboxylic acid tert-butyl ester (2.71 g, 5.00 mmol) in CH$_2$Cl$_2$ (20 mL). Add trifluoroacetic acid (5.88 mL, 77.79 mmol). Stir at room temperature for one hour and then add 5 N NaOH to pH=8-10. Collect a white/yellow precipitate via vacuum filtration, and wash the solid with EtOAc followed by Et$_2$O. Dry the solid overnight in vacuo at about 50° C. to give 2.21 g (>99%) of the title compound. ES/MS m/z ($^{35}$Cl) 442.0 [M+1]$^+$.

Example 26a

5-[4-(Azetidin-3-yloxy)-3-methoxy-phenyl]-2-(4-chloro-phenyl)-6,7-dihydro-5H-thiazolo[5,4-c]pyridin-4-one, hydrochloride salt Dissolve 3-{4-[2-(4-chloro-phenyl)-4-oxo-6,7-dihydro-4H-thiazolo[5,4-c]pyridin-5-yl]-2-methoxy-phenoxy}-azetidine-1-carboxylic acid tert-butyl ester (3.33 g, 6.16 mmol) in CH$_2$Cl$_2$ (21 mL) and add trifluoroacetic acid (7.25 mL). Stir for one hour at room temperature and then add 1 N NaOH to adjust to pH=8-10. Extract with EtOAc (3×50 mL) and wash with water (2×50 mL). Collect an off-white solid via vacuum filtration (2.15 g, 79%). Re-dissolve a portion of the crude material (300 mg, 0.68 mmol) in CHCl$_3$ and add 4 N HCl/dioxane solution (about 200 µL). Remove the organic solvent via reduced pressure to dryness to give 316 mg of the titled compound. ES/MS m/z ($^{35}$Cl) 442.0 [M+1]$^+$.

Prepare the free base lactam compounds in the table below, Preparation 52 to 55, by essentially following the procedure as described in Example 26.

| Prep | Product (Chemical Name) | ES/MS m/z |
|---|---|---|
| 52 | 2-(Azetidin-3-yloxy)-5-[2-(4-chloro-phenyl)-4-oxo-6,7-dihydro-4H-thiazolo[5,4-c]pyridin-5-yl]-benzonitrile | $^1$H NMR (300 MHz, CD$_3$OD) δ: 8.0 (d, 2H, J = 9.0), 7.72 (d, 1H, J = 2.6), 7.61 (dd, 1H, J = 6.4 9.0), 7.50 (d, 2H, J = 8.6), 6.90 (dd, 1H, J = 8.9), 5.19 (m, 1H), 4.10 (t, 2H, J = 7.0), 3.98 (m, 2H), 3.74 (m, 2H), 3.28 (m, 2H). |

-continued

| Prep | Product (Chemical Name) | ES/MS m/z |
|---|---|---|
| 53 | 5-[4-(Azetidin-3-yloxy)-3-chloro-phenyl]-2-(4-chloro-phenyl)-6,7-dihydro-5H-thiazolo[5,4-c]pyridin-4-one | ($^{35}$Cl) 446 [M + 1]$^+$ |
| 54 | 5-[4-(Azetidin-3-yloxy)-3-fluoro-phenyl]-2-(4-chloro-phenyl)-6,7-dihydro-5H-thiazolo[5,4-c]pyridin-4-one | ($^{35}$Cl) 430 [M + 1]$^+$ |
| 55 | 5-[4-(Azetidin-3-yloxy)-phenyl]-2-(4-chloro-phenyl)-6,7-dihydro-5H-thiazolo[5,4-c]pyridin-4-one | ($^{35}$Cl) 412 [M + 1]$^+$ |
| 56 | 5-[4-(Azetidin-3-yloxy)-3-methoxy-phenyl]-2-(4-fluoro-phenyl)-6,7-dihydro-5H-thiazolo[5,4-c]pyridin-4-one | 426 [M + 1]$^+$ |

Example 27

2-(4-Chloro-phenyl)-5-[3-methoxy-4-(1-methyl-azetidin-3-yloxy)-phenyl]-6,7-dihydro-5H-thiazolo[5,4-c]pyridin-4-one Mix 5-[4-(azetidin-3-yloxy)-3-methoxy-phenyl]-2-(4-chloro-phenyl)-6,7-dihydro-5H-thiazolo[5,4-c]pyridin-4-one (3.1 g, 7.01 mmol) with anhydrous MeOH (100 mL) and treat with acetic acid (4.0 mL, 69.8 mmol) and formaldehyde (1.6 mL, 21.30 mmol, as a solution in water). Stir the mixture at room temperature for 30 min and then treat with sodium cyanoborohydride (1.3 g, 19.6 mmol). Stir the mixture at room temperature overnight and concentrate in vacuo. Partition the resulting residue between CH$_2$Cl$_2$ (100 mL) and saturated NaHCO$_3$ (100 mL). Remove the organic solution and extract the aqueous phase with additional CH$_2$Cl$_2$ (2×100 mL). Combine the organic solutions and wash with water (50 mL), then dry, filter, and concentrate in vacuo. Purify the crude material by flash chromatography, using 8% MeOH (2M NH$_3$)/CH$_2$Cl$_2$ as eluent, to give 1.6 g (50%) of the title compound as a yellow solid. ES/MS m/z ($^{35}$Cl) 456 [M+1]$^+$.

Example 27a 2-(4-Chloro-phenyl)-5-[3-methoxy-4-(1-methyl-azetidin-3-yloxy)-phenyl]-6,7-dihydro-5H-thiazolo[5,4-c]pyridin-4-one, hydrochloride salt Dissolve 2-(4-chloro-phenyl)-5-[3-methoxy-4-(1-methyl-azetidin-3-yloxy)-phenyl]-6,7-dihydro-5H-thiazolo[5,4-c]pyridin-4-one (2.1 g, 4.6 mmol) in CH$_2$Cl$_2$ (25 mL) and treat with 4.0 M HCl (1.3 mL, 5.2 mmol, solution in diethyl ether). Stir the solution for 10 min. Add additional diethyl ether (25 mL) and isolate the precipitate by filtration. Wash the solid with diethyl ether and dry under vacuum to give 2.08 g (92%) of the title compound. ES/MS m/z ($^{35}$Cl) 456 [M+1]$^+$.

Example 28

2-(4-Chloro-phenyl)-5-[4-(1-isopropyl-azetidin-3-yloxy)-3-methoxy-phenyl]-6,7-dihydro-5H-thiazolo[5,4-c]pyridin-4-one, hydrochloride salt Dissolve 5-[4-(azetidin-3-yloxy)-3-methoxy-phenyl]-2-(4-chloro-phenyl)-6,7-dihydro-5H-thiazolo[5,4-c]pyridin-4-one (1.0 g, 2.26 mmol) and acetone (250 µL, 3.39 mmol) in dry 1,2-dichloroethane. Add sodium triacetoxyborohydride (1.0 g, 4.53 mmol) and stir overnight at room temperature. Add 1 N NaOH solution to the reaction mixture and extract with CH$_2$Cl$_2$ (2×25 mL). Combine the organic portions and wash with water (2×25 mL). Dry the organic layer with Na$_2$SO$_4$, then filter, and concentrate in vacuo. Triturate the crude yellow solid with Et$_2$O and filter. Wash the solid with Et$_2$O several times and re-dissolve in CHCl$_3$. Add 1 N HCl/Et$_2$O solution (1.5 mL) and remove the solvent in vacuo to give 630 mg (53%) of the title compound. ES/MS m/z ($^{35}$Cl) 484.2 [M+1]$^+$.

Prepare the compounds in the table below, Examples 29 to 35, by essentially following the procedure as described in Example 28 using the appropriate free base and the appropriate aldehyde, respectively.

| Ex | Product (Chemical Name) | ES/MS m/z |
|---|---|---|
| 29 | 2-(4-Chloro-phenyl)-5-[4-(1-cyclobutyl-azetidin-3-yloxy)-3-methoxy-phenyl]-6,7-dihydro-5H-thiazolo[5,4-c]pyridin-4-one, hydrochloride salt | ($^{35}$Cl) 496.0 [M + 1]$^+$ |
| 30 | 2-(4-Chloro-phenyl)-5-{3-methoxy-4-[1-(2-methoxy-ethyl)-azetidin-3-yloxy]-phenyl}-6,7-dihydro-5H-thiazolo[5,4-c]pyridin-4-one, hydrochloride salt | ($^{35}$Cl) 500.2 [M + 1]$^+$ |
| 31 | 5-[2-(4-Chloro-phenyl)-4-oxo-6,7-dihydro-4H-thiazolo[5,4-c]pyridin-5-yl]-2-(1-methyl-azetidin-3-yloxy)-benzonitrile, hydrochloride salt | ($^{35}$Cl) 451 [M + 1]$^+$ |
| 32 | 5-[3-Chloro-4-(1-methyl-azetidin-3-yloxy)-phenyl]-2-(4-chloro-phenyl)-6,7-dihydro-5H-thiazolo[5,4-c]pyridin-4-one, hydrochloride salt | ($^{35}$Cl) 460 [M + 1]$^+$ |
| 33 | 2-(4-Chloro-phenyl)-5-[3-fluoro-4-(1-methyl-azetidin-3-yloxy)-phenyl]-6,7-dihydro-5H-thiazolo[5,4-c]pyridin-4-one, hydrochloride salt | ($^{35}$Cl) 444 [M + 1]$^+$ |
| 34 | 2-(4-Chloro-phenyl)-5-[4-(1-methyl-azetidin-3-yloxy)-phenyl]-6,7-dihydro-5H-thiazolo[5,4-c]pyridin-4-one, hydrochloride salt | ($^{35}$Cl) 426.2 [M + 1]$^+$ |
| 35 | 2-(4-Fluoro-phenyl)-5-[3-methoxy-4-(1-methyl-azetidin-3-yloxy)-phenyl]-6,7-dihydro-5H-thiazolo[5,4-c]pyridin-4-one, hydrochloride salt | 440.2 (M + 1)$^+$ |

Example 36

2-(4-Chloro-phenyl)-5-{4-[1-(2-hydroxy-ethyl)-azetidin-3-yloxy]-3-methoxy-phenyl}-6,7-dihydro-5H-thiazolo[5,4-c]pyridin-4-one, hydrochloride salt Dissolve 5-[4-(azetidin-3-yloxy)-3-methoxy-phenyl]-2-(4-chloro-phenyl)-6,7-dihydro-5H-thiazolo[5,4-c]pyridin-4-one (500 mg, 1.13 mmol) and 2,5-dihydroxy-1,4-dioxane (68 mg, 1.13 mmol) in dry 1,2-dichloroethane (6.66 mL). Add sodium triacetoxyborohydride (500 mg, 2.26 mmol) and stir overnight at room temperature. Add 1 N NaOH solution to the reaction mixture and extract with CH$_2$Cl$_2$ (2×25 mL). Combine the organic portions and wash with water (2×25 mL). Dry the organic layer with Na$_2$SO$_4$, filter, and concentrate in vacuo. Purify on HPLC, 4.6×75 mm XBridge® C18, Eluent: Reverse phase gradient 5-95% MeOH/water 0.1% TFA in 10 min, 2 mL/min. Re-dissolve the acquired material in CHCl$_3$ and add 1 N HCl/Et$_2$O solution (160 µL), followed by concentration in vacuo to give 65 mg (13%) of the title compound. ES/MS m/z ($^{35}$Cl) 486.0 [M+1]$^+$.

Example 37

2-(4-Chloro-phenyl)-5-[4-(1-cyclopropyl-azetidin-3-yloxy)-3-methoxy-phenyl]-6,7-dihydro-5H-thiazolo[5,4-c]pyridin-4-one, hydrochloride salt Mix molecular sieves (60 mg, type 3A), 5-[4-(azetidin-3-yloxy)-3-methoxy-phenyl]-2-(4-chloro-phenyl)-6,7-dihydro-5H-thiazolo[5,4-c]pyridin-4-one (1.00 g, 2.26 mmoles), [(1-ethoxycyclopropyl)oxy]trimethylsilane (685.2 μL, 3.39 mmoles), and acetic acid (648 μL, 11.31 mmoles) in dry methanol (11.4 mL). Reflux the mixture for 3 h. Cool the mixture to room temperature, add sodium cyanoborohydride (300 mg, 4.53 mmol) and slowly warm to 40° C. for 1 h. Cool the mixture and add 1 N NaOH solution. Extract the aqueous layer with CHCl$_3$ (3×25 mL). Purify on HPLC, 4.6×150 mm Kromasil® silica, Eluent: 40% THF/heptane 0.1% N,N'-dimethylethylamine, 1 mL/min. Re-dissolve the material in CHCl$_3$ and add 1 N HCl/Et$_2$O solution (750 μL). Concentrate the solvent in vacuo to give 375 mg (34%) of the title compound. ES/MS m/z ($^{35}$Cl) 482.2 [M+1]$^+$.

Example 38

2-(4-Chloro-phenyl)-5-{3-methoxy-4-[1-(3,3,3-trifluoro-propionyl)-azetidin-3-yloxy]-phenyl}-6,7-dihydro-5H-thiazolo[5,4-c]pyridin-4-one Dissolve 5-[4-(azetidin-3-yloxy)-3-methoxy-phenyl]-2-(4-chloro-phenyl)-6,7-dihydro-5H-thiazolo[5,4-c]pyridin-4-one (100 mg, 0.226 mmol), and 3,3,3-trifluoropropionyl chloride (137 mg, 0.905 mmol) in dry pyridine (754.3 μL). Add 4-N,N-dimethylpyridine (2.9 mg, 0.0226 mmol) and stir the solution overnight. Add NaHSO$_4$ solution and extract with EtOAc (2×20 mL). Combine the organic portions and wash with water (10 mL). Dry the organic solution with Na$_2$SO$_4$, filter, and concentrate in vacuo. Purify the crude material on silica gel chromatography, using an isocratic gradient of 80% EtOAc in hexanes, to give 88 mg (70%) of the title compound as a yellow solid. ES/MS m/z ($^{35}$Cl) 552.8 [M+1]$^-$.

We claim:

1. A compound of formula

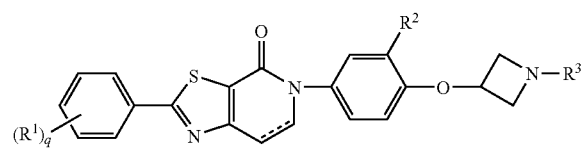

wherein

"-----" is absent or is optionally a bond;
q is 1 or 2;
R$^1$ is independently selected from hydrogen, —C$_1$-C$_2$ alkyl, halo, hydroxy, —C$_1$-C$_2$ haloalkyl, —C$_1$-C$_3$ alkoxy, cyano, —O—C$_3$-C$_4$ cycloalkyl, and —OC$_1$-C$_2$ haloalkyl;
R$^2$ is selected from the group consisting of hydrogen, —C$_1$-C$_3$ alkyl, hydroxy, —C$_1$-C$_3$ alkoxy, cyano, —C$_1$-C$_2$ haloalkyl, —OC$_1$-C$_2$ haloalkyl, and halo;
R$^3$ is selected from the group consisting of hydrogen, —C$_1$-C$_4$ alkyl, —C$_2$-C$_4$ haloalkyl, —C$_2$-C$_4$ alkylOH, —C$_3$-C$_6$ cycloalkyl, —CH$_2$C$_3$-C$_6$ cycloalkyl, —C—C$_4$ alkyl-O—C$_1$-C$_4$ alkyl, —C(O)C$_1$-C$_4$ alkyl, —C(O)C$_1$-C$_4$ haloalkyl, —CH$_2$-thiazole, phenyl, benzyl, tetrahydrothiopyranyl, and tetrahydropyranyl, wherein the cycloalkyl, tetrahydrothiopyranyl, tetrahydropyranyl or thiazolyl group is optionally substituted with one or two groups independently selected from the group consisting of halo, hydroxy, C$_1$-C$_2$ alkyl, and —C$_1$-C$_2$ haloalkyl; or a pharmaceutically acceptable salt, enantiomer, diastereomer or mixture thereof.

2. A compound of formula

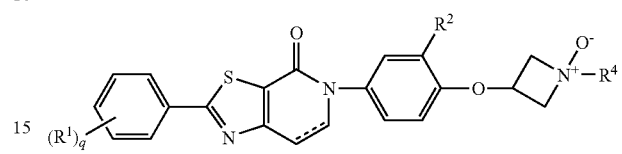

wherein:

"-----" is absent or is optionally a bond;
q is 1, or 2;
R$^1$ is independently selected from hydrogen, —C$_1$-C$_2$ alkyl, halo, hydroxy, —C$_1$-C$_2$ haloalkyl, —C$_1$-C$_3$ alkoxy, cyano, —O—C$_3$-C$_4$ cycloalkyl, and —OC$_1$-C$_2$ haloalkyl;
R$^2$ is selected from the group consisting of hydrogen, —C$_1$-C$_3$ alkyl, hydroxy, —C$_1$-C$_3$ alkoxy, cyano, —C$_1$-C$_2$ haloalkyl, —OC$_1$-C$_2$ haloalkyl, and halo;
R$^4$ is selected from the group consisting of —C$_1$-C$_4$ alkyl, —C$_2$-C$_4$ alkylOH, and —C$_3$-C$_6$ cycloalkyl wherein the cycloalkyl group is optionally substituted with one or two groups independently selected from the group consisting of halo, and —C$_1$-C$_2$ alkyl; or a pharmaceutically acceptable salt, enantiomer, diastereomer or mixture thereof.

3. A compound according to claim 1 wherein R$^1$ is chloro, fluoro, trifluoromethyl, methoxy, or cyclopropoxy or a pharmaceutically acceptable salt, enantiomer, diastereomer or mixture thereof.

4. A compound according to claim 1 wherein R$^2$ is H, —OCH$_3$, F, Cl, or cyano or a pharmaceutically acceptable salt, enantiomer, diastereomer or mixture thereof.

5. A compound according to claim 1 wherein R$^3$ is selected from the group consisting of hydrogen, methyl, cyclopropyl, cyclobutyl, —C(O)CH$_2$CH$_3$, isopropyl, —CH$_2$CH$_2$OH, 2-fluoroethyl, 2,2-difluoroethyl, and —C(O)CH$_3$, or a pharmaceutically acceptable salt, enantiomer, diastereomer or mixture thereof.

6. A compound according to claim 1 wherein R$^3$ is selected from the group consisting of hydrogen, methyl, cyclopropyl, —CH$_2$cyclopropyl, cyclobutyl, —C(O)CH$_2$CH$_3$, isopropyl, —CH$_2$CH$_2$OH, fluoroethyl, 2,2-difluoroethyl, and —C(O)CH$_3$, or a pharmaceutically acceptable salt, enantiomer, diastereomer or mixture thereof.

7. A compound according to claim 1 wherein R$^3$ is hydrogen or C$_1$-C$_3$ alkyl, cyclopropyl, cyclobutyl, or isopropyl, or a pharmaceutically acceptable salt, enantiomer, diastereomer or mixture thereof.

8. A compound according to claim 1 wherein
R$^1$ is chloro, methoxy, cyclopropoxy, fluoro, or trifluoromethyl;
q is 1 or 2;
R$^2$ is H, —CN or —OCH$_3$; and
R$^3$ is hydrogen, —CH$_3$, —CH$_2$CH$_2$OH, —CH$_2$CH$_2$F, —CH$_2$CHF$_2$, isopropyl, cyclopropyl, —CH$_2$cyclopropyl, or cyclobutyl wherein the cyclopropyl or cyclobutyl group is optionally substituted with one or two groups independently selected from the group consisting of fluoro and methyl, or a pharmaceutically acceptable salt, enantiomer, diastereomer or mixture thereof.

9. A compound according to claim 1 wherein
R$^1$ is chloro;
q is 1;
R$^2$ is H, —OCH$_3$; and
R$^3$ is hydrogen, —CH$_3$, cyclopropyl, or cyclobutyl wherein the cyclopropyl or cyclobutyl group is optionally substituted with a group selected from the group consisting of fluoro, hydroxy and methyl, or a pharmaceutically acceptable salt, enantiomer, diastereomer or mixture thereof.

10. A compound selected from the group consisting of:
5-[4-(azetidin-3-yloxy)-3-methoxy-phenyl]-2-(4-chloro-phenyl)-5h-thiazolo[5,4-c]pyridin-4-one,
2-(4-chloro-phenyl)-5-[4-(1-cyclobutyl-azetidin-3-yloxy)-3-methoxy-phenyl]-5h-thiazolo[5,4-c]pyridin-4-one,
2-(4-chloro-phenyl)-5-[4-(1-cyclopropyl-azetidin-3-yloxy)-3-methoxy-phenyl]-5h-thiazolo[5,4-c]pyridin-4-one,
5-[4-(1-acetyl-azetidin-3-yloxy)-3-methoxy-phenyl]-2-(4-chloro-phenyl)-5h-thiazolo[5,4-c]pyridin-4-one,
2-(4-chloro-phenyl)-5-[3-methoxy-4-(1-methyl-azetidin-3-yloxy)-phenyl]-5h-thiazolo[5,4-c]pyridin-4-one,
5-[4-(azetidin-3-yloxy)-3-methoxy-phenyl]-2-(4-chloro-phenyl)-6,7-dihydro-5h-thiazolo[5,4-c]pyridin-4-one,
2-(4-chloro-phenyl)-5-[3-methoxy-4-(1-methyl-azetidin-3-yloxy)-phenyl]-6,7-dihydro-5h-thiazolo[5,4-c]pyridin-4-one,
2-(4-chloro-phenyl)-5-[4-(1-isopropyl-azetidin-3-yloxy)-3-methoxy-phenyl]-6,7-dihydro-5h-thiazolo[5,4-c]pyridin-4-one;
2-(4-chloro-phenyl)-5-[4-(1-cyclobutyl-azetidin-3-yloxy)-3-methoxy-phenyl]-6,7-dihydro-5h-thiazolo[5,4-c]pyridin-4-one;
2-(4-chloro-phenyl)-5-{3-methoxy-4-[1-(2-methoxy-ethyl)-azetidin-3-yloxy]-phenyl}-6,7-dihydro-5h-thiazolo[5,4-c]pyridin-4-one;
2-(4-chloro-phenyl)-5-{4-[1-(2-hydroxy-ethyl)-azetidin-3-yloxy]-3-methoxy-phenyl}-6,7-dihydro-5h-thiazolo[5,4-c]pyridin-4-one;
2-(4-chloro-phenyl)-5-[4-(1-cyclopropyl-azetidin-3-yloxy)-3-methoxy-phenyl]-6,7-dihydro-5h-thiazolo[5,4-c]pyridin-4-one; and
2-(4-chloro-phenyl)-5-{3-methoxy-4-[1-(3,3,3-trifluoro-propionyl)-azetidin-3-yloxy]-phenyl}-6,7-dihydro-5h-thiazolo[5,4-c]pyridin-4-one.

11. The compound 5-[4-(azetidin-3-yloxy)-3-methoxy-phenyl]-2-(4-chloro-phenyl)-5H-thiazolo[5,4-c]pyridin-4-one

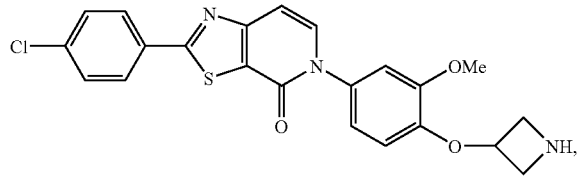

or a pharmaceutically acceptable salt thereof.

12. The compound 2-(4-chloro-phenyl)-5-[4-(1-cyclobutyl-azetidin-3-yloxy)-3-methoxy-phenyl]-5H-thiazolo[5,4-c]pyridin-4-one,

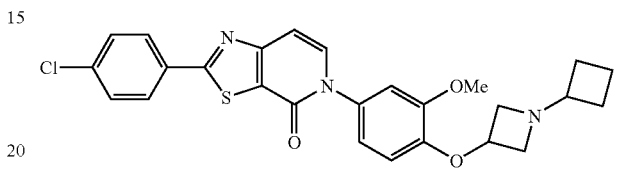

or a pharmaceutically acceptable salt thereof.

13. The compound 2-(4-chloro-phenyl)-5-[3-methoxy-4-(1-methyl-azetidin-3-yloxy)-phenyl]-5H-thiazolo[5,4-c]pyridin-4-one

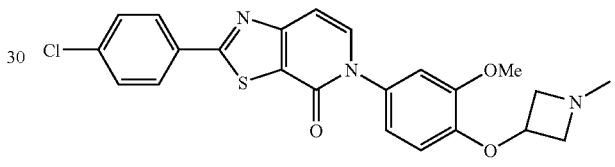

or a pharmaceutically acceptable salt thereof.

14. The compound 2-(4-Chloro-phenyl)-5-[4-(1-isopropyl-azetidin-3-yloxy)-3-methoxy-phenyl]-6,7-dihydro-5H-thiazolo[5,4-c]pyridin-4-one,

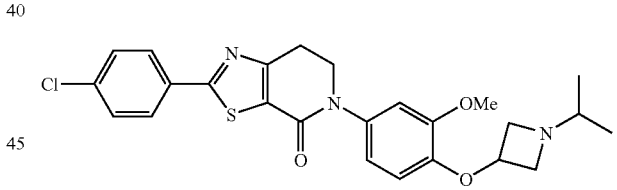

or pharmaceutically acceptable salt thereof.

15. A compound according to claim 1 which is the hydrochloric acid salt or the oxalic acid salt.

16. A pharmaceutical composition comprising a compound of claim 1 and a pharmaceutically acceptable carrier and/or diluent.

* * * * *

UNITED STATES PATENT AND TRADEMARK OFFICE
CERTIFICATE OF CORRECTION

| | | |
|---|---|---|
| PATENT NO. | : 8,049,013 B2 | Page 1 of 1 |
| APPLICATION NO. | : 12/515432 | |
| DATED | : November 1, 2011 | |
| INVENTOR(S) | : Kevin Matthew Gardinier et al. | |

It is certified that error appears in the above-identified patent and that said Letters Patent is hereby corrected as shown below:

At column 45, line 65, in Claim 1, delete "—C—$C_4$" and insert -- —C-$C_4$ --, therefor.

Signed and Sealed this
Twenty-seventh Day of December, 2011

David J. Kappos
*Director of the United States Patent and Trademark Office*